(12) United States Patent
Hilscher et al.

(10) Patent No.: US 7,207,080 B2
(45) Date of Patent: *Apr. 24, 2007

(54) DENTAL CLEANING DEVICE

(75) Inventors: Alexander Hilscher, Kronberg (DE);
Hansjörg Reick, Steinbach (DE);
Martin Stratmann, Frankfurt (DE);
Peter Trawinski, Weiterstadt (DE);
Wolfgang Vorbeck, Idstein-Eschenhahn (DE); Armin Schwarz-Hartmann, Wendelsheim (DE)

(73) Assignee: Braun GmbH, Kronberg (DE)

( * ) Notice: Subject to any disclaimer, the term of this patent is extended or adjusted under 35 U.S.C. 154(b) by 1227 days.

This patent is subject to a terminal disclaimer.

(21) Appl. No.: 10/241,274

(22) Filed: Sep. 10, 2002

(65) Prior Publication Data

US 2003/0101526 A1 Jun. 5, 2003

(30) Foreign Application Priority Data

Dec. 4, 2001 (DE) ................. 101 59 395

(51) Int. Cl.
*A61C 17/22* (2006.01)
*A46B 13/02* (2006.01)

(52) U.S. Cl. .......................... 15/22.1; 15/28
(58) Field of Classification Search ........... 15/22.1, 15/22.2, 23, 28
See application file for complete search history.

(56) References Cited

U.S. PATENT DOCUMENTS

| | | | |
|---|---|---|---|
| 3,220,039 A | 11/1965 | Dayton et al. | |
| 3,571,544 A | 3/1971 | Sheehan | |
| 3,782,799 A | 1/1974 | Hansen | |
| 3,802,420 A | 4/1974 | Moffat et al. | |
| 3,810,147 A | 5/1974 | Lichtblau | |
| 3,904,841 A | 9/1975 | Swatman | |
| 4,156,620 A | 5/1979 | Clemens | |
| 4,352,098 A | 9/1982 | Stephen et al. | |
| 4,365,376 A | 12/1982 | Oda et al. | |
| 4,371,118 A | 2/1983 | Sontheimer et al. | |
| 4,413,199 A | 11/1983 | Fischer | |
| 4,506,400 A | 3/1985 | Klein | |
| 4,595,850 A | 6/1986 | Woog | |
| 4,704,602 A | 11/1987 | Asbrink | |
| 4,736,207 A | 4/1988 | Siikaria et al. | |
| 4,820,152 A | 4/1989 | Warrin et al. | |
| 4,827,550 A | 5/1989 | Graham et al. | |
| 4,914,376 A | 4/1990 | Meyer | |

(Continued)

FOREIGN PATENT DOCUMENTS

CN 2048697 12/1989

(Continued)

OTHER PUBLICATIONS

Use instructions to Braun D5 electric toothbrush Type 4726 on sale in United States, circa 1991 (3 sheets-cover and pp. 8-11) including description of "Travel lock" switch.

(Continued)

*Primary Examiner*—Randall Chin
(74) *Attorney, Agent, or Firm*—Fish & Richardson P.C.; Edward S. Podszus

(57) ABSTRACT

An electric toothbrush with a removable brush section having a transponder communicating with a handle portion of the toothbrush via a non-contacting inductive coupling.

20 Claims, 11 Drawing Sheets

U.S. PATENT DOCUMENTS

| | | |
|---|---|---|
| 5,065,137 A | 11/1991 | Herman |
| 5,099,536 A | 3/1992 | Hirabayashi |
| 5,184,959 A | 2/1993 | Oryhon et al. |
| 5,263,218 A | 11/1993 | Giuliani et al. |
| 5,289,604 A | 3/1994 | Kressner |
| 5,337,435 A | 8/1994 | Krasner et al. |
| 5,341,534 A | 8/1994 | Serbinski et al. |
| 5,381,576 A | 1/1995 | Hwang |
| 5,392,028 A | 2/1995 | Pichl |
| 5,561,881 A | 10/1996 | Klinger et al. |
| 5,576,693 A | 11/1996 | Tyren et al. |
| 5,577,285 A | 11/1996 | Drössler |
| 5,760,580 A | 6/1998 | Tyren |
| 5,784,742 A | 7/1998 | Giuliani et al. |
| 5,812,065 A | 9/1998 | Schrott et al. |
| 5,943,723 A | 8/1999 | Hilfinger et al. |
| 5,974,615 A | 11/1999 | Schwarz-Hartmann |
| 6,029,303 A | 2/2000 | Dewan |
| 6,177,870 B1 | 1/2001 | Lian et al. |
| 6,195,828 B1 | 3/2001 | Fritsch |
| 6,202,242 B1 | 3/2001 | Salmon et al. |
| 6,227,853 B1 | 5/2001 | Hansen et al. |
| 6,367,108 B1 | 4/2002 | Fritsch et al. |
| 6,531,873 B1 | 3/2003 | Wohlrabe |
| 2002/0129454 A1 | 9/2002 | Hilscher et al. |
| 2003/0101526 A1 | 6/2003 | Hilscher et al. |
| 2003/0115694 A1 | 6/2003 | Pace |
| 2004/0255409 A1 | 12/2004 | Hilscher et al. |
| 2005/0000044 A1 | 1/2005 | Hilscher et al. |
| 2005/0011025 A1 | 1/2005 | Hilscher et al. |

FOREIGN PATENT DOCUMENTS

| | | |
|---|---|---|
| CN | 2124686 | 12/1992 |
| CN | 2149877 | 12/1993 |
| CN | 2332378 | 8/1999 |
| DE | 24 13 524 | 10/1975 |
| DE | 28 26 08 C2 | 6/1983 |
| DE | 37 08 801 | 9/1988 |
| DE | 3708801 A1 | 9/1988 |
| DE | 40 36 373 C2 | 11/1990 |
| DE | 40 36 479 | 5/1992 |
| DE | 42 43 219 A1 | 12/1992 |
| DE | 3880015 T2 | 9/1993 |
| DE | 44 22 086 C1 | 6/1994 |
| DE | 43 05 013 | 8/1994 |
| DE | 195 06 129 | 2/1995 |
| DE | 195 18 935 | 5/1995 |
| DE | 296 08 164 | 5/1996 |
| DE | 196 27 752 A1 | 7/1996 |
| DE | 297 09 865 U1 | 6/1997 |
| DE | 299 18 858 U1 | 9/1999 |
| DE | 198 32 607 | 5/2000 |
| DE | 199 21 677 | 11/2000 |
| DE | 199 23 104 A1 | 11/2000 |
| DE | 199 53 651 | 5/2001 |
| EP | 024 992 | 6/1984 |
| EP | 046 169 | 8/1984 |
| EP | 285 915 | 10/1988 |
| EP | 440 051 | 8/1991 |
| EP | 391 967 B1 | 8/1992 |
| EP | 294 548 B1 | 4/1993 |
| EP | 624 079 | 10/1993 |
| EP | 634 151 | 1/1995 |
| EP | 787 469 | 8/1997 |
| EP | 0787469 A1 | 8/1997 |
| EP | 848 921 | 12/1997 |
| GB | 2082713 | 3/1982 |
| JP | 04-087127 | 3/1992 |
| JP | 04-269906 | 9/1992 |
| JP | 05-269024 | 10/1993 |
| JP | 08-000358 | 1/1996 |
| JP | 08-117030 | 5/1996 |
| JP | 08-275961 | 10/1996 |
| JP | 11-318951 | 11/1999 |
| SU | 749380 | 7/1980 |
| SU | 1542539 | 2/1990 |
| SU | 1674789 | 9/1991 |
| WO | 97/24079 | 7/1997 |
| WO | 98/24527 | 6/1998 |
| WO | 98/55274 | 12/1998 |
| WO | 00/74591 | 6/2000 |
| WO | 00/39768 | 7/2000 |
| WO | 00/42584 | 7/2000 |
| WO | 00/47128 | 8/2000 |
| WO | WO 00/74591 | 12/2000 |
| WO | 01/91603 | 6/2001 |
| WO | 01/08591 | 8/2001 |

OTHER PUBLICATIONS

Color photographs of Bausch & Lomb "Interplak" Model PB-4B style Handpiece with travel protection switch and Toothbrush attachment (handpiece stamped "1D IA", believed circa 1992 on sale in the United States) (2 sheets with 7 views).

Package rear and bottom panels of Bausch & Lomb Interplak Model PB-4B, marked © 1990 (color copy, 1 sheet).

Product use instructions to Bausch & Lomb Interplak travel-style "Voyager" model TK-2 marked © 1991 (6 photocopied sheets containing cover and pp. 1-10).

Color photographs of Bausch & Lomb "Interplak" Model PB-6 style Handpiece with waterproof electronic travel protection switch (believed circa 1992 on sale in the United States) (6 views).

Package rear and bottom panels of Bausch & Lomb Interplak Model PB-6, marked © 1992 (color copy, 1 sheet).

"RFID Made Easy" Handbook by EM Microelectronic-Marin SA, 2074 Marin, Switzerland, copr. 2000 and dated Mar. 2001, Rev. C/350, pp. 1-33.

Herzer, Gieselher, "Der große Lauschangriff auf Ladendiebe" [transl: "The great surveillance of Shoplifters"] in Physikalische Blätter [transl: Physics Letters] vol. 57 (2001), No. 5, pp. 43-48.

Finkenzeller, Klaus, "RFID-Handbuch, Grundlagen und praktische Anwendungen induktiver Funkanlagen, Transponder und kontaktloser Chipkarten" [Trans: "RFID Handbook, Fundamentals and practical Applications to inductive radio Communications, Transponders and Contactless Chip Cards"], Carl Hanser Verlag München, 2nd Edition, Chapter 3, pp. 29 to 58 w/ title page and Impressum, Contents pp. vii-xviii, and Appendices 15.2 "Standards" and 15.3 "Literature" on pp. 393 to 406.

Applicants' U.S. Appl. No. 10/662,237, filed Sep. 15, 2003 pending, publication expected circa Mar. 15, 2005.

PCT Search Report of PCT/EP01/02844 corresponding to U.S. Appl. No. 10/662,237, filed Aug. 1, 2001.

PCT Search Report of PCT/EP01/02862 corresponding to co-pending U.S. Appl. No. 09/811,080, filed Jul. 25, 2001.

PCT Search Report of PCT/EP02/01724 corresponding to co-pending U.S. Appl. No. 10/241,274, filed Jul. 10, 2002.

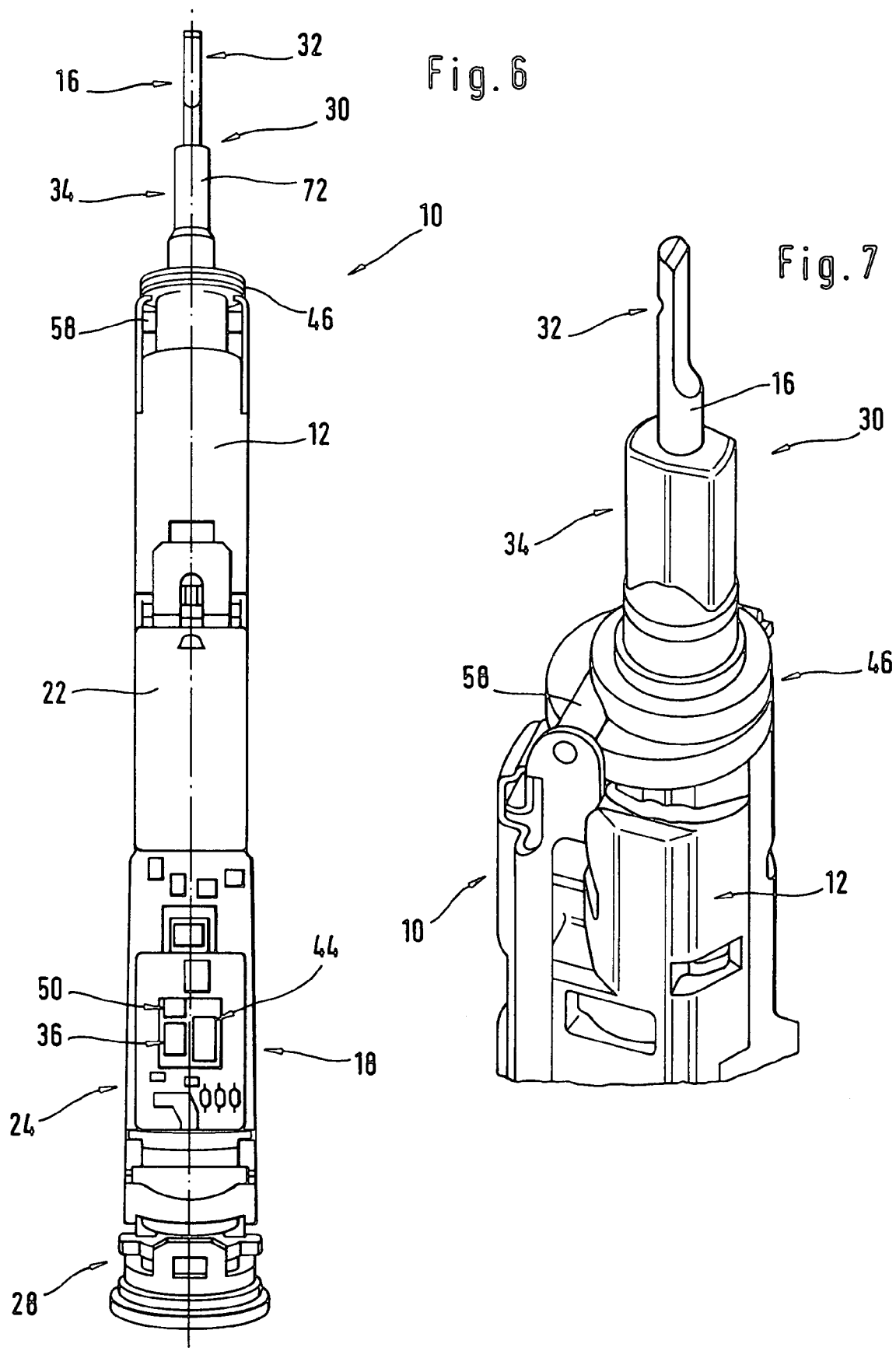

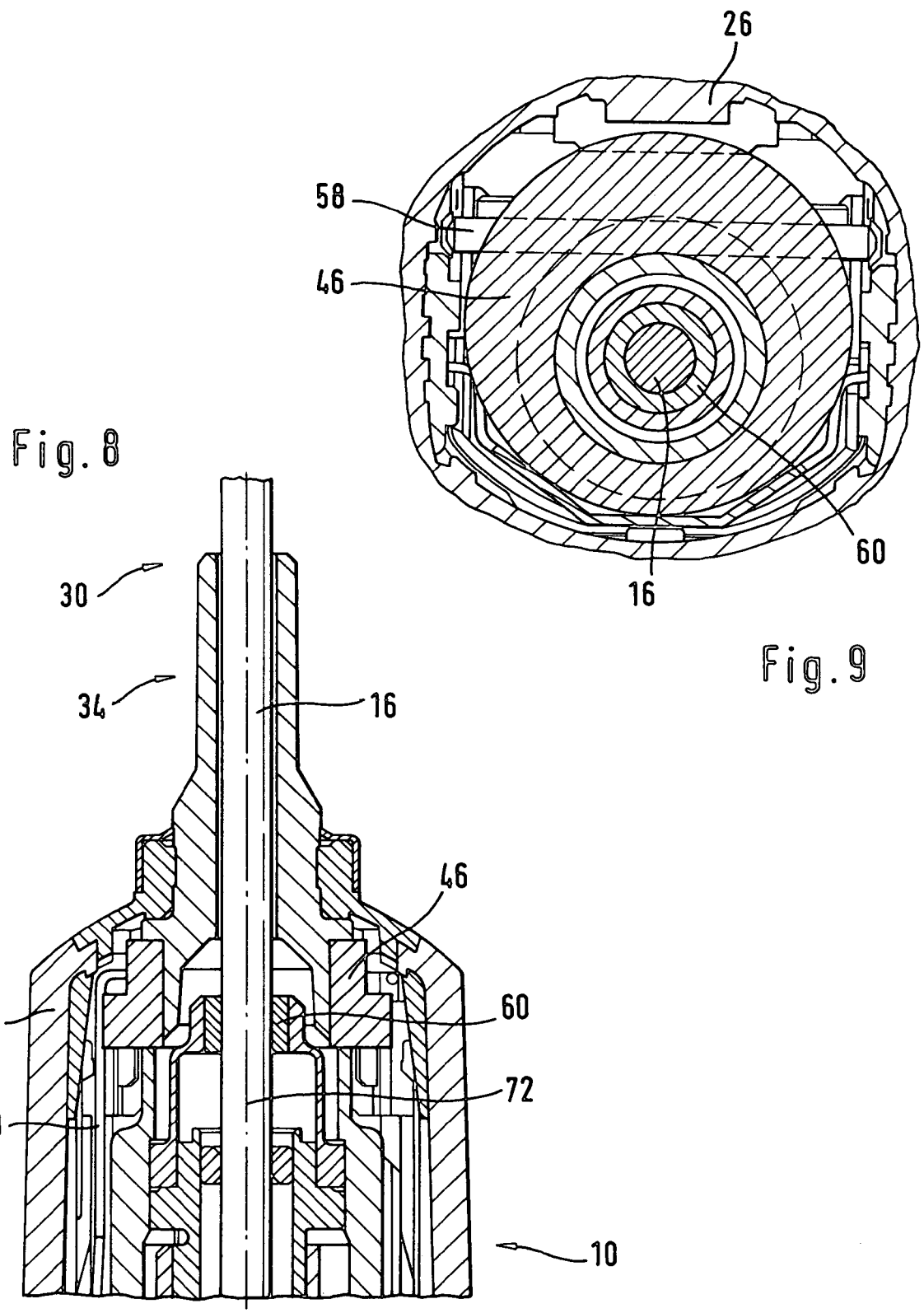

DENTAL CLEANING DEVICE

This application claims the benefit under 35 USC §119 of a priority application filed in Germany, serial number 10159395.3, filed Dec. 4, 2001, the entire contents of which are hereby incorporated in their entirety.

TECHNICAL FIELD

This invention relates to an electrical dental cleaning device. The invention relates in particular to the handle section of such a dental cleaning device which has a coupling device for the coupling of various or different brush sections, a drive mechanism for driving the respectively coupled brush section, and a control device. The invention further relates to the brush sections, particularly brush attachments, for such a handle section.

BACKGROUND

Devices for brushing or cleaning teeth such as electrical toothbrushes or electrical oral irrigators customarily have a grip or a handle section or handhold to which a variety of cleaning tools such as brush attachments, jet nozzles, interproximal brushes or brush sections are attachable, thus enabling several users to use the dental cleaning device with their own, in particular person-related cleaning tools. Such electrical toothbrushes are known, for example, from DE 19627752 A1 or EP 0624079 B1.

From DE 299 15 858 U1 a dental cleaning device is known in which each of the different toothbrushes can be inserted only into its assigned receptacle in a console. This then starts the program provided for this particular toothbrush. Particularly children find it however difficult to locate the individual opening for insertion of their personal toothbrush and mating engagement of the plug. Furthermore, this console involves high complexity of manufacture, considering that it requires the provision of a plurality of different receptacles and each of the toothbrushes has a different plug assigned to its own receptacle.

In a further device disclosed in U.S. Pat. No. 5,184,959, each hand toothbrush is assigned its own accommodating slot in a housing, so that each toothbrush can be assigned an individual brushing time signal via the housing. This arrangement is very elaborate from the manufacturing point of view without providing for the detection and storage of user-specific data of the tooth cleaning operation.

Such dental cleaning devices are capable of improvement on many counts. One problem encountered is in particular that in storage-battery-operated toothbrushes the storage battery may become depleted prematurely. This may happen, for example, in cases where the toothbrush is not properly stowed away in a travel case or the like, so that the drive mechanism turns on accidentally. Furthermore, it may happen that the handle section is not always coupled with the correct brush attachments, so that as a result of the lack of compatibility the handle section, for example, the coupling portions, may be damaged particularly in the area of the drive train, or a proper cleaning function is not assured, likewise for lack of compatibility.

Furthermore, dental cleaning devices, namely electrically operated toothbrushes comprising a handle section and an attachable brush section in which the handle section has in a recess of its housing a mechanically actuatable switch which, as the case may be, is covered by a water-tight protective foil such that a switching contact of said switch is actuated by means of an extension of the plastic housing of the brush section when the brush section is attached to the handle section, were also launched on the market in the USA in approximately 1992 from the company Bausch & Lomb, model Interplak®, e.g., the PB-6. Once the switching contact has been actuated by an attached brush section, the drive mechanism of the toothbrush can be switched on by means of an ON switch on the handhold. These features are provided presumably for safety reasons because, unlike many other handle sections on electrical toothbrushes, the drive shaft on the previously mentioned toothbrush oscillates back and forth in the direction of the longitudinal axis. The stroke of the shaft is so considerable that switching on the handle section without an attached brush section could lead to risk of injury because the drive shaft makes a stroking movement similar to a sewing needle on a sewing machine.

From DE 28 26 008 C2 there is known a switch for actuating an electrical toothbrush with a permanent magnet arranged on an annular actuating member, said annular actuating member being axially displaceably arranged on the housing. The permanent magnet of the annular actuating member activates or deactivates a magnetically sensitive switch, e.g. a reed relay, which is arranged in the interior of the housing of the toothbrush. The annular actuating member can be pulled off the housing of the toothbrush, enabling the housing and the actuating member to be cleaned with ease after its removal. Removing the actuating member has the simultaneous effect of making it impossible for the electrical toothbrush to be switched on, thus preventing a toothbrush with the actuating member detached from switching on by itself when it is being transported in a case and the batteries or storage batteries becoming depleted accidentally.

The above-mentioned features for providing a certain travel security function have not proven a success in practice however because in the case of the Interplak® solution considerable force is required to attach and detach the brush section to and from the handle section in order to actuate the switching contact provided in the handle section. A further problem is that the switching contacts become dirty and that a great effort is needed to produce a dirt- or water-proof covering over the switching contact. The detachable switching ring in patent specification DE 28 26 008 C2 is intended likewise to perform a security function when traveling, but here there is a problem in that the detached switching ring can get lost, particularly on journeys, and that it is then impossible to set the handhold in operation even with full batteries or storage batteries. Furthermore, these known solutions for providing security when on journeys display little flexibility as regards other comfort functions such as the automatic adaptation of a handle section's operating parameters to a specific brush section or the user-specific collection and storage of cleaning data or the like.

From EP 0 848 921 A1 there is also known a brush for DIY use and a manufacturing method therefor, in which a tag as data memory is irremovably fastened in the brush itself, namely between a bristle carrier and a cup-shaped holding element. It is then intended to use the tag to store data concerning safety standards, maximum speed, country of origin, manufacturer's brand, article number, connection diameter and, for example, a barcode that can be read by an electronic reading system at the cash-desk of a DIY store, for example. The tag can be made in particular of aluminum or a heat-resistant plastic material because the brushes are exposed to very high temperatures during use. This tag is evidently an aluminum or plastic disk that has a surface loaded with optically readable information and is irremovably connected with the brush body. The disadvantage of such codes, however, is that they have a rather small storage capacity and cannot be re-programmed. Their readability also assumes that the code is freely accessible in optical terms, which is not the case in all applications.

Further, there is known a multiplicity of electronic article security systems in which security tags comprising, for example electrical resonant circuits or soft magnetic sensor strips, are affixed to the articles and excited by electromagnetic fields in gates installed in shop exit areas. If the articles have not been paid for, i.e., the security tags are still active, a signal is detected and an alarm emitted. Pertinent details can be found, for example, in the article "Der große Lauschangriff auf Ladendiebe" by Gieselher Herzer, Physikalische Blätter 57 (2001), No. 5, pages 43 to 48.

A sub-case of these systems are the systems referred to as RFID (radio frequency identification) systems, which find application on noncontacting chip cards and, more recently, on motor vehicle keys or refuse bins in order, in the latter case, to enable invoices to be issued according to the actual emptying of the bins.

Such systems are known, for example, from U.S. Pat. No. 5,812,065, WO 00/42584, U.S. Pat. No. 6,177,870, WO 00/39768, DE 199 53 651 A1 or WO 98/24527, the system disclosed in the last mentioned specification being used in an electronic toy to exchange data between a figure, which is equipped with a transponder, and a base unit, which is equipped with a reader.

SUMMARY

It is an object of the present invention to provide an improved handle section of an electrical dental cleaning device and improved brush sections therefor, which avoid the disadvantages of the prior art, develop it further and afford additional advantages. In particular the invention aims to provide a comfortable safety device with the possibility of activating further specific functions and/or preventing improper use of the dental cleaning device.

In a handle section of an electrical dental cleaning device comprising a coupling device for the mechanical coupling of a brush section, a drive mechanism for the brush section and a control function for the drive mechanism, said control function including an operation inhibiting function that can be activated and deactivated by an enabling function in particular of the brush section, this object is accomplished essentially in that the handle section includes a reading function and a coil as coupling function for the non-contacting transmission and reading of one or more items of information or data of the enabling function, the inhibiting function being activated or deactivated in response to an output signal of the reading function. The advantage of these features over the prior art is that they enable comfortable handling when coupling and decoupling the handle section and the brush section, eliminate the need for mechanical actuation by the brush section of components provided in the handle section for activating/deactivating the inhibiting function, and lay the basis for implementing further user-friendly functions. Furthermore, it is unnecessary to remove switch mechanisms or other components from the handle section in order to achieve a security function during travel. It is noted below that the terms "handle section" of an electrical dental cleaning device, "brush section" or the like may not refer only to an electrically operated toothbrush but also to other electrically operated dental cleaning devices such as oral irrigators, interproximal cleaners or the like, in which a handle section is adapted to be coupled to a cleaning section which is used either by a specific user or is a disposable item. To this extent the terms brush section, brush attachment, plug-in brush, spare brush are interchangeable with the terms cleaning section, jet nozzle and interproximal cleaner.

According to one embodiment of the invention it is an advantage for the reading function and/or coupling function to be activatable via a switch-on function of the handle section, in particular a switch-on function for the drive mechanism.

It is also expedient for the reading function or coupling function to transfer and read data, provided the brush section is mechanically coupled to the handle section.

In this context, it is an advantage that provision is made for the coupling function to operate inductively.

The coil is preferably arranged in a portion of the handle section adjacent to the coupling device or also in the area of the coupling device itself.

It is also expedient for the coil to have one or several turns that encompass or enclose a longitudinal axis of the handle section, preferably an axis of rotation of a drive shaft driven by the drive mechanism in the handle section.

Provision is also made for the turn area of the coil to define with a rotary or longitudinal axis of the handle section an included angle of between about 140 degrees and about 40 degrees, preferably 90 degrees plus or minus 10 degrees.

In an exceptional case it may also be expedient for the enabling function to be associated with the handle section itself, in particular is fastened in or on a housing of the handle section.

Furthermore it is possible, by means of the drive mechanism, for a drive shaft to be set in at least one alternating rotary motion about an axis of rotation or one rotary motion about an axis of rotation and/or in a swivel motion about a swivel axis positioned essentially perpendicular to the axis of rotation.

Advantageously, the reading function, the control function and the operation inhibiting function are part of an ASIC. In some cases of application it may also be expedient however for these functions to be implemented as discrete functions or, as far as possible, for them to be implemented by means of suitable software in a micro-controller or the like.

To accomplish the object identified in the foregoing, the brush section with a drivable brush head as well as a mating coupling device for coupling mechanically to a handle section comprising a coupling device, a drive mechanism and an operation inhibiting function of an electrical toothbrush, with an enabling function associated with the brush section for activating or deactivating the inhibiting function is characterized in that the enabling function of the brush section comprises a non-contacting data carrier and a coil as a coupling means for the non-contacting transmission of one or more items of data.

The data carrier or the coupling means of the brush section is activatable preferably via a switch-on means of the handle section or a switch-on function associated therewith, preferably for switching on the drive mechanism.

The data carrier or the coupling means preferably transmits data provided the brush section is mechanically coupled to the handle section.

It is an advantage for the coupling means to operate inductively.

The coil is preferably arranged in a portion of the mating coupling device or in a portion of the brush section adjacent thereto.

The coil preferably has one or several turns which encompass or enclose a longitudinal axis of the brush section or an axis of rotation of a plug-on shaft in the brush section.

The turn area of the coil preferably defines, together with a rotary or longitudinal axis of the brush section, an included angle of between about 140 and 40 degrees, preferably 90 degrees plus or minus 10 degrees.

It is an advantage in this connection for a profiled sleeve to be provided on the brush section, which sleeve is received in a tubular shank of the brush section, and for the readout/transmission function or the parts or components performing this function to be arranged on the profiled sleeve or connected therewith. Furthermore, the shank of the brush section can also receive a plug-on shaft.

The non-contacting data carrier may be constructed as a transponder, preferably a passive transponder without its own energy supply.

Provision is advantageously made for the transponder to have a data memory for digital data, preferably with a storage capacity of between $10^0$ bit and $10^4$ bit, approximately.

The present invention is also directed to an electrical dental cleaning device with a handle section in combination with a brush section of the type described in the foregoing. In this arrangement the data transmitted between brush section and handle section may include not only data for activating the enabling function but also data specifically for the individual brush section, for operating parameters for the operation of the brush section or handle section or specifically for the individual user.

Advantageously, the digital data may be subjected to a coding/detecting function.

Provision is furthermore made for one or more data items to be transmitted from the brush section to the handle section and/or vice versa.

In some embodiments, energy is suitably transmitted from the handle section to the brush section to activate the passive transponder.

Provision is preferably made for the handle section and the brush section to be inductively coupled by means of the coils for the exchange of data or for the transmission of data and/or transmission of energy.

According to another aspect of the invention, on a handle section of an electrical dental cleaning device, provision is advantageously made for a control device having an operation inhibiting device that can be deactivated via non-contacting data exchange or data transmission by an enabling means on the cleaning tool. The cleaning tool of the type initially referred to possesses an enabling means to deactivate the inhibiting device of the handle section via non-contacting data exchange or data transmission between the brush section and the handle section. These features thus provide protection against unintentional switching on of the dental cleaning device. The drive mechanism of the handle section can only be switched on when a compatible cleaning tool providing an enabling function is attached to the handle section and the handle section's inhibiting function is deactivated as the result. Unintentional switching on in a travel case or the like can easily be prevented by removing the cleaning tool from the handle section. Unintentional premature depletion of the drive's storage battery is thus impossible. Additional design or mechanical approaches for implementing a switch-on lock, for example on the switch of the handle section, can be rendered unnecessary. Provision can be advantageously made for the inhibiting device to be deactivated solely by the enabling device of the cleaning tool, particularly only when the cleaning tool is properly coupled to the handle section. This can be achieved in that the enabling device on the cleaning tool and a detecting device for the enabling device on the handle section are constructed and coordinated such that the enabling device is effective preferably in a predetermined orientation and/or position relative to the detecting device and hence to the handle section. To prevent the handle section, particularly the drive train or its coupling, from being damaged by plugging on unsuitable brush attachments, the enabling device can have an additional code or transmit coded data by means of which the cleaning tool is identifiable. The handle section thus has a coding/detecting device or decoding means which detects or decodes the code of the respectively attached cleaning tool. The inhibiting device is only deactivated when the correct code is present and a corresponding signal is produced. The handle section thus detects the individual cleaning tool attached at that moment and controls the enabling of the drive mechanism according to the detected cleaning tool. The code can be queried generally at predetermined intervals. In a particular embodiment of the invention the coding/detecting device is only activated when an ON switch of the handle section, for example of the electric drive mechanism, is actuated. This has the advantage that the current consumption of the required electronic components is minimized. To switch on the dental cleaning device the user actuates the ON/OFF switch of the control device or electric motor as usual. However, the electric motor or drive mechanism is not directly set in motion by actuating the switch but first the coding and/or detecting device is activated, which then sets the motor of the handle section in operation provided a compatible and suitably coded brush attachment is coupled to the handle section. Ultimately, therefore, activating the coding and/or detecting device by means of the ON/OFF switch sets the drive mechanism of the handle section only indirectly in operation, namely when the enabling element of the brush section deactivates the inhibiting device of the handle section. If no brush section is attached or coupled to the handle section or if there is a non-compatible brush section on the handle section, the coding and/or detecting device will not detect a suitable code when the ON/OFF switch of the handle section is actuated, or the enabling element missing from the brush attachment will be unable to deactivate the inhibiting device of the handle section so that in this case the handle section of the electric motor driven toothbrush cannot be put in operation. One of the advantages afforded by providing for such activation of the coding and/or detecting device by means of the ON/OFF switch is that the coding and/or detecting device needs to be supplied with electrical current preferably only when the switch of the handle section is switched on or off, being otherwise inactive or passive. It is also possible of course to activate the coding and/or detecting device at regular or irregular intervals during operation of the toothbrush in order to check the presence of a compatible, that is, correctly coded brush attachment, also when the switch is not being switched on or off. This is a preferable possibility to correct a mis-detection of a brush attachment. If, for whatever reasons, the handle section was switched on by the device without a brush section attached (with the switch actuated), e.g., due to a temporary electronic malfunction or strong fields of interference, the handle section can be switched off again with the next activation of the device. If, when the dental cleaning operation is over, the ON/OFF switch is actuated again in order to switch off the drive mechanism of the handle section, the drive mechanism will be directly stopped by this actuation and, if applicable, the inhibiting device deactivated so that when the ON/OFF switch of the handle section is switched on again subsequently the described process can be repeated. Furthermore, the coding and/or detecting device is constructed to operate in non-contacting fashion. This has the advantage of avoiding interference due to soiled contact faces or wear as a result of frequent attaching and detaching or elaborate sealing measures. It is also possible for the handle section to comprise a signal receiver receiving from the cleaning tool a coded signal or a signal deactivating the inhibiting device. The handle section may also be equipped with a signal transmitter sending an interrogation or activation signal to the enabling function of the cleaning tool, whereupon the latter is activated energetically and sends the coded signal or enabling signal back. The emission of the coded signal or enabling signal by the enabling function of the cleaning tool may take place by a corresponding active or passive signal transmitter or a suitable acting member.

The coding or configuration of the enabling element of the cleaning tool(s) may be implemented by incorporating it in the cleaning tool itself or in a portion or part of the cleaning tool as, for example, a colored ring or profiled ring of the type described, for example, in WO 99/20202, which shall be deemed to be incorporated in the disclosure content of the present application by express reference, or in a corresponding device.

A further approach includes the provision of an electrically operating detecting device for detecting an electrical coding, meaning the presence of the enabling element of the respectively coupled cleaning tool. The cleaning tool sends a not coded or a coded electrical signal to the handle section, meaning to a signal receiver provided thereon, thus enabling the respective cleaning tool to be identified. It is also possible for the handle section to send initially an interrogation signal to the cleaning tool which is coded or modified by the cleaning tool and sent back subsequently. Provision can also be made for a transmit or radio device for detecting the respectively attached cleaning tool by means of electromagnetic waves. In particular a transponder may be associated with the cleaning tool. The handle section initially emits electromagnetic waves for energy supply to the generally passive transponder. The transponder stores the energy and sends an individual ID back to a detector in the handle section which detects the ID and correspondingly identifies the cleaning tool and deactivates the inhibiting function.

The cleaning tool is thus characterized by the provision of a magnetic, electrical and/or electro-magnetically operating coding device or an enabling element of this type. Another characteristic feature may include the provision of a signal receiver for receiving a signal from the dental cleaning device and of a signal transmitter for transmitting a coded signal to the dental cleaning device, there being inserted preferably a coding device between the signal receiver and the signal transmitter for coding the received signal. The coding device or the enabling element is preferably constructed as a separate component suitable for detachment from the remaining part of the cleaning tool or for replacement. The advantage thereby achieved is that the cleaning tool has to be manufactured in only one embodiment. By mounting the separate coding device or enabling function the cleaning tools are coded on an individual basis and are assignable to a particular type of handle section. However, the coding device constructed as enabling element may also be integrated in the cleaning tool when it is desirable to provide solely a travel security function or detect incompatible cleaning tools. The coding device or enabling element is arranged preferably in the area of the connection or coupling between the cleaning tool and the handle section.

This facilitates the reading of the coding, meaning the detection of the enabling element by the recognition device on the handle section. In particular, the enabling element or coding device may be integrated in a ring arranged at the end of the cleaning tool close to the handle section, being in particular snap-fitted thereto by positive engagement therewith. The various configurations of the recognition devices may be provided singularly or in combination. The same applies to the various configurations of the coding device or enabling element on the cleaning tool.

Apart from protecting the handle section against inadvertent turning on and improper use of incompatible cleaning tools, a coding of the cleaning tools and its detection by the handle section may be utilized to advantage for performing further functions. In this context, provision can be made for the handle section to control one or preferably several functions of the dental cleaning device in dependence upon the respective cleaning tool detected. Assuming that each user of the handle section has his or her own cleaning tool, particularly the control device of the handle section may establish automatically, by referring to the detected coding on the cleaning tool, which user is currently using the dental cleaning device. There is no need on the user's part to inform the dental cleaning device of its current user as by pressing a button and the like. The operating parameters of the device can be adapted to the individual user automatically. This results in a maximum of user friendliness. In particular the control device is capable of adapting operating parameters such as cleaning frequency, cleaning speed and cleaning period or threshold value or recommended range of application pressure automatically to the individual user identified. A variety of user profiles can be set and stored, one of which is used by the control device after, at the beginning of cleaning, the coding of the cleaning tool being currently used has been detected and the respective user has been established. To this effect the coding and/or detecting device has issued a corresponding signal to the control device. Where electrical toothbrushes are used, it is possible, for example, for the motor speed to be reduced from the usual speed for adults when a child is the user, so that a gentler cleaning operation is performed for the child. In addition, the control device may vary, responsive to a signal from the coding and/or detecting device, the duration of a timer according to the user identified, setting the timer to two minutes for children and to three minutes for adults, for example. The type of timer signal could also be modified, as by selecting a tune for children and a buzzer tone for adults. A further solution offering itself is to store data for new timer tunes in the brush attachment and transmit them from the brush attachment to the handle section where they may also be stored, as the case may be.

It is also possible to store, process and indicate as on a display user-specific data such as cleaning frequency, cleaning speed, cleaning period, time interval between cleaning operations or application pressure automatically in response to a corresponding signal from the detecting device. This also results in enhanced user comfort.

The handle section hence detects, i.e., identifies, the individual user indirectly by referring to the cleaning tool used or its coding. Provision may also be made for a specific function control in dependence upon the particular type of cleaning tool used. For instance, operating parameters of the handle section may be varied automatically when a brush attachment with specific properties such as high or low hardness is used. Equally, another operating program may be run when a cleaning tool of different type as, for example, an interproximal cleaning tool, a tool for gum massage or a tongue cleaner is attached to the handle section. Rotational frequency, recommended cleaning period, driving motion, cleaning frequency, cleaning speed, application pressure threshold value, etc. can be suitably adapted in response to the individual and/or person-related exchangeable cleaning tool.

Still further, by identifying an individual cleaning or brushing tool or refill unmistakably it is possible to establish its state of wear precisely, for example, by evaluating the history of this particular cleaning tool, in particular the time of past uses. Where cleaning tools with chemical additives are used, their "use by" date can be identified by the date of manufacture contained in the coding. Predetermined cleaning or maintenance intervals can be indicated.

According to a preferred embodiment an RFID (radio frequency identitication) reaching device is provided in the handle section of the toothbrush in order to implement the enabling function, a reading device being understood to be the detecting device for the data of a transponder provided in the brush section and transmitted in non-contacting manner. The RFID reading device and the transponder or some other non-contacting data carrier each have a coupling element, which can be a coil or also a microwave antenna for example, whereby data, clock pulses or energy are exchanged via these coupling elements between the reading device and the non-contacting data carrier. It is thus possible, by means of the reading device, which is also referred to as a transceiver (transmitter/receiver) to receive data or information from the transponder. Conversely, it is also possible to use the reading device to write data into the transponder. Thus, for example, the possibility exists to write into the transponder data concerning the user of the individual brush section or also data concerning the period of cleaning or use for an individual brush section so that when a certain maximal cleaning period has elapsed the user can be reminded, for example, to replace the brush section with a new one. Generally, energy is transmitted from the reading device to the transponder when the transponder is of the passive type, meaning a transponder without an energy supply of its own. The energy transmitted from the reading device to the transponder is then used for activation of the transponder. In the event of an active transponder being used, meaning a transponder with its own energy supply, for example a button cell as a battery or the like, it will be understood, of course, that the transmission of energy to activate the transponder is not necessary. An inductive or magnetic coupling is preferably provided in the given case for electrical dental cleaning devices as an element for the non-contacting coupling of the reading device and transponder. In the relevant literature such couplings are referred to as inductive radio systems or inductively coupled short range devices. The operating frequency in the given case of application preferably lies at 13.56 MHz. The transponder itself can be configured as a 1-bit or multi-bit transponder. The transmission of information or data between the transponder and the reading device is preferably performed by means of a load modulation in the transponder, for which purpose a load resistor is switched on or off in the transponder at a cycle frequency or certain pulse train, thus producing a reaction or feedback in the reading device via the inductive coupling, enabling the data to be transmitted from the transponder to the reading device and vice versa.

According to another aspect of the invention, the enabling element or enabling function on the cleaning tool for deactivating the operation inhibiting device or function can be configured in the simplest embodiment of the coding and/or detecting device or function in such manner that only the presence or absence (1-bit information) of a replacement brush on the handle section is detectable. To this effect, for example, an acting member may be arranged in the brush which corresponds with a reacting member in the handle section, in such manner that with the cleaning tool and the handle section in coupled condition the reacting member receives from the acting member a preferably digital signal and deactivates, for example, the inhibiting device provided, so that the handle section and hence also the cleaning tool can be set in operation by means of the drive mechanism. This provides a simple travel security function for the handle section preventing the handle section from operating when the cleaning tool with its acting member is not coupled thereto as described above. Accordingly it is sufficient to decouple the cleaning tool from the handle section to activate the travel security function. Further steps for blocking, for example, the ON/OFF switch of the handle section or any other devices are not necessary. It is also helpful to arrange such an acting member in the cleaning tool, which member, in coupled condition, corresponds or communicates with a reacting member in the handle section so that operation of the handle section with incompatible cleaning tools can be prevented, because the manufacturer does not as a rule equip such incompatible cleaning tools with an acting member that would be capable of communicating with the reacting member of the handle section. Mechanical problems and risks incurred by the use of incompatible brush attachments can be eliminated. This represents a coding and/or detecting device or function in its simplest form, it is of relatively straightforward construction and permits merely a decision to be made as to whether a cleaning tool is coupled to the handle section or whether the cleaning tool coupled to the handle section is compatible.

For exceptional situations provision may also be made for the acting member typically provided in the cleaning tool, for example, a transponder or the like or the coding device to be made available to the end user as a separate, isolated part or to provide it on the handle section itself. This approach offers itself, for example, when the end user is already in possession of a handle section equipped with an operation inhibiting device but has a household supply of brushing or cleaning tools available which are not equipped with an enabling element or an acting member for deactivation of the inhibiting function of the handle section or handhold. To assure usability of these typically older replacement cleaning tools which, while being mechanically compatible with the more recent handhold, do not have as yet an enabling element which would be suited for communication with, and deactivation of, the inhibiting device provided in the handle section, a meaningful approach may therefore be to make the enabling element or the acting member or transponder available to the end user as a separate component, providing for these exceptional situations a fastening device on the handle section to fasten the enabling element there. This makes it possible, for example, for the end user to fasten this enabling element or acting member directly to the handle section or handhold equipped with the inhibiting device, as on the exterior of the housing in the area of the reacting member of the handle section, and to deactivate for such special or exceptional cases the inhibiting device of the handle section by arranging the acting member on the handle section itself and not on the cleaning tool. As a result, the handle section is also operable with cleaning tools which, while being mechanically compatible, are not as yet equipped with an enabling function or an acting member communicating with the inhibiting device. This solution may also be contemplated when for cost reasons, for example, not all of the replacement cleaning tools compatible or mechanically mating with the handle section or handhold are equipped with such an enabling element, a coding device or an acting member. It will be understood, of course, that the solution involving the fastening of the enabling element directly to the handle section as by its user is an exceptional situation, and that as a rule the enabling element should be arranged on the brush section or cleaning section.

Still further, the coding/detecting device may also be configured so as to enable the coupling of a cleaning tool allowing for a few possibilities of distinction of cleaning tools (multi-bit information). While the coding and/or detecting device or function initially described allows, for example, only a yes/no decision, that is, a decision as to whether or not a compatible cleaning tool is coupled to the handle section, a modified coding and/or detecting device or function allowing, for example, the identification of two, four or six different codings of the cleaning tool enables further functions to be performed in addition to the travel security function. Thus, for example, it is possible for the handle section to identify whether a toothbrush designed for adults (hard bristles) or a toothbrush designed for children (soft bristles) is coupled to the handle section, whether an interproximal cleaner is used in lieu of a toothbrush, or also to distinguish between other parameters. Where applicable, the respectively detected coding can be used for selectively driving the control device for the drive mechanism controlling, for example, the speed of the drive such as the rotational frequency, or the recommended cleaning period or the like. In the event of provision being made for a coding or a coding and/or detecting device or function with few (between about two and about ten) possibilities of distinction, it is however not possible as yet to identify an individual cleaning tool from a million of commercially available cleaning tools. With these limited possibilities of distinction it is at best possible to identify a special type of cleaning tool (child toothbrush, adult toothbrush, interproximal brush, dental flosser, each configured as an attachment to the handle section) and to make a distinction between a few individualized cleaning or brushing tools.

When it is desired to detect with the coding and/or detecting device or function every single individual cleaning tool produced by the manufacturer which is adapted to be coupled to the handle section as a compatible part, allowance need be made for a multiplicity of possibilities of distinction (multi-bit information) in the range from about $10^6$ to about $10^{12}$, for which purpose a transponder or similar electronic device is typically used. In this case the identification of an individual cleaning tool supplied by the manufacturer and coupled to the handle section is possible. In addition to the possibilities previously mentioned in connection with simpler coding solutions, this provides the prerequisite forte ability to determine, for example, the degree of wear of the cleaning tool more accurately by evaluating the tool history. Where replacement cleaning tools with chemical additives are used, the date of manufacture indicated in the coding enables "use by" dates to be identified or predetermined cleaning or maintenance intervals of the cleaning tool to be indicated or complied with.

Regardless of how simple or complex the coding of the cleaning tool and the coding and/or detecting device or function, the enabling function for the inhibiting function on the handle section assures in each case a travel security function by decoupling the in particular compatible cleaning tool from the handle section, thereby preventing operation of the handle section. Setting the handle section in operation is likewise prevented with any one of these coding solutions, irrespective of whether a 1-bit or multi-bit solution is employed, provided the cleaning tool does not have a coding or enabling element in the first place. When such a cleaning tool which is not coded or not equipped with an enabling element is coupled to the handle section, the reacting member, transmitter, receiver or similar reading device positioned in the handle section is unable to communicate with the acting member, receiver, transmitter, transponder or similar device not provided in the incompatible cleaning tool, so that precisely as in the case of a cleaning tool which is compatible but not coupled to the handle section, the presence of this incompatible cleaning tool is not recognized on the handle section, as a result of which the handle section cannot be set in operation due to the absence of the enabling element and the attendant lack of possible deactivation of the inhibiting device.

In the basically most straightforward embodiment of the coding of the cleaning tool or the coding and/or detecting device or function in the handle section of the electric dental cleaning device, care has to be taken only to ensure that the coding and/or detecting device or function in the handle section is in a position to recognize whether or not a proper, i.e., compatible cleaning tool is coupled to the handle section. If such a proper, i.e., compatible cleaning tool is not coupled to the handle section, the handle section cannot be set in operation, because the cleaning tool has no associated enabling element suitable for deactivation of an inhibiting device provided in the handle section. By contrast, when a compatible cleaning tool equipped with the enabling element or the proper coding is coupled to the handle section, it is not later than on actuation of the ON/OFF switch on the handle section that the presence of the proper coding or of the enabling element will be detected by means of a detecting device in the handle section, causing deactivation of the inhibiting device and setting the handle section in operation, so that the cleaning end, for example, the brush head of the cleaning tool, is set in operation by the drive mechanism of the handle section.

The present invention also relates to a method of operating an electrical tooth cleaning or tooth brushing device comprised of a handle section and a cleaning tool adapted to be attached or coupled thereto, as for example, a brush attachment or the like, wherein the handle section and the cleaning tool communicate with each other in coupled condition or transmit or exchange data in non-contacting fashion, or devices being provided in the handle section which are in a position to detect whether a cleaning tool is coupled to the handle section and/or whether the cleaning tool coupled to the handle section is a cleaning tool compatible with the handle section. When no cleaning tool is coupled to the handle section, this information is used for suppressing an activation of the electric drive of the handle section as by means of the ON switch provided on the handle section. This may be accomplished by an operation inhibiting device in the handle section. Hence it is not possible to set the handle section in operation with the cleaning tool not coupled or attached thereto, whereby a comfortable travel security function is provided. A further feature characteristic of the method is that the cleaning tool includes an enabling function signaling to a detecting device arranged in the handle section that the cleaning tool is coupled to the handle section and the inhibiting device can be deactivated so that the dental cleaning appliance can be set in operation by turning on the electric drive. If, however, the cleaning tool is not equipped with such an enabling element, even in coupled condition of cleaning tool and handle section the drive of the handle section cannot be activated because in the absence of an enabling element on the cleaning tool it has to be assumed that a cleaning tool incompatible with the handle section is involved.

Further embodiments of the method also include the step of coding the different cleaning tools to be coupled to the handle section on a person-specific, cleaning-tool-specific or similar basis, hence enabling the handle section or handhold to be informed, via a corresponding coding/detecting device, not only of the coupled or non-coupled condition of a cleaning tool or a compatible cleaning tool but also of the type of cleaning tool used or the individual using the cleaning tool, so that corresponding parameters or also operating parameters of the handle section can be set or stored as person- and/or cleaning-tool-specific data. These individual approaches are explained in detail within the scope of the description of the devices and also pertain to the present method. It will be understood that the terms "operation inhibiting device" and "coding and/or detecting device or means" or "recognition device" as well as the terms "enabling element" and "coding device or coding means or device and function" are used as synonyms and may be used interchangeably.

Further objects, advantages, features and application possibilities of the present invention will become apparent from the subsequent description of embodiments illustrated in the accompanying drawings.

DESCRIPTION OF DRAWINGS

FIG. 6 is a schematic perspective view of an embodiment of the handle section with the housing removed therefrom.

FIG. 7 is a schematic perspective view of the forward portion of a further embodiment of the handle section with the housing removed therefrom.

FIG. 8 is a longitudinal sectional view of a further embodiment of the coupling end of an embodiment of the handle section.

FIG. 9 is a cross-sectional view of the handle section of FIG. 7, with the section plane being arranged approximately in the region of the coil substantially perpendicular to the longitudinal axis or axis of rotation of the drive shaft.

DETAILED DESCRIPTION

Figure 1:
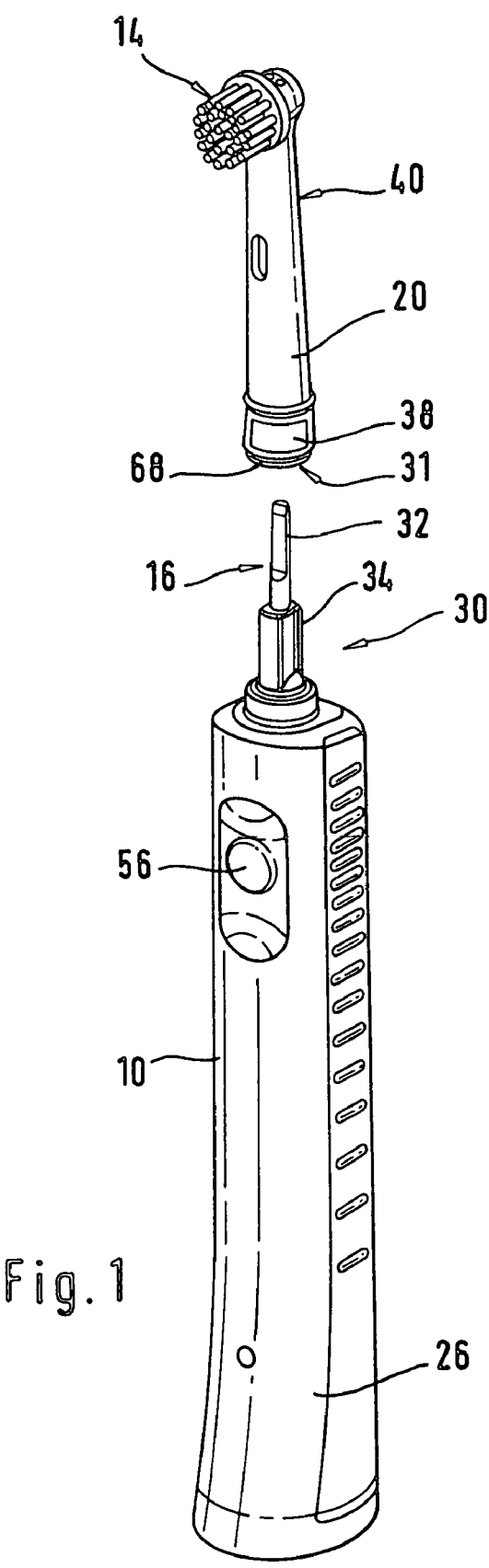
FIG. 1 is a perspective view of an electrical toothbrush having a handle section and a brush attachment attachable thereto.
Figure 2:
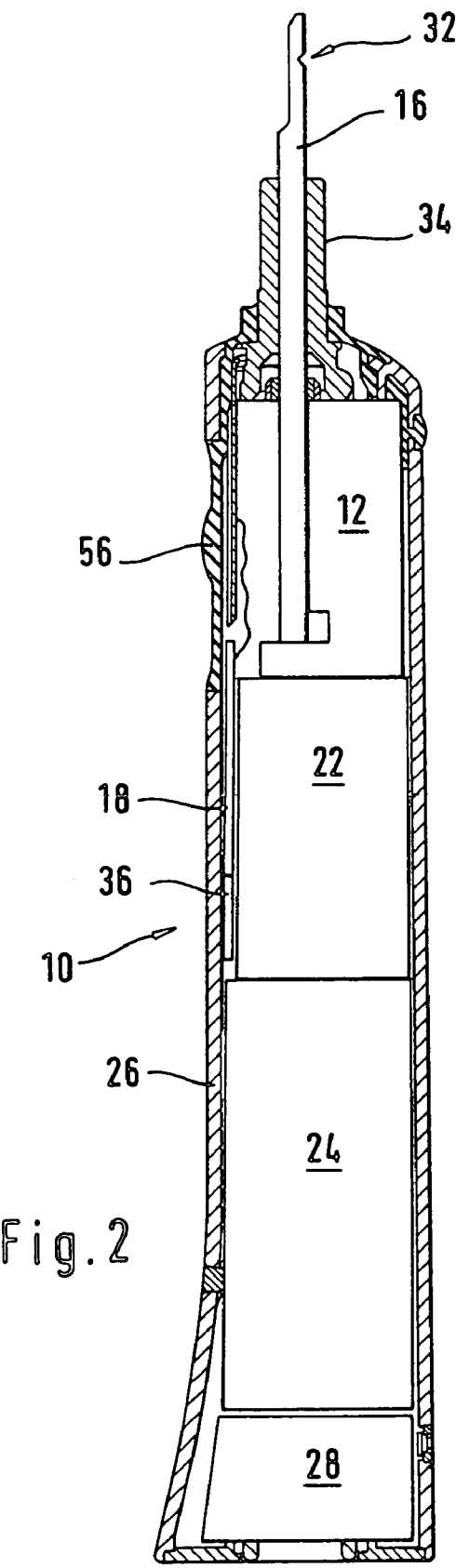
FIG. 2 is a schematic longitudinal sectional view of the handle section of the electrical toothbrush of FIG. 1, showing its housing and, arranged therein, the drive motor with gearing and drive shaft, the storage battery for the drive motor, and the charging module for the storage battery.

The electrical toothbrush shown in the Figures has a handle section 10 with a closed housing 26 accommodating, among other components and as illustrated in FIG. 2, in a manner known in the art an electric motor 22, a power supply, in particular a storage battery 24 adapted to be coupled to a charging station through a charging module 28 disposed at the bottom, and a control device or controller 18 which may include a printed circuit board with a microprocessor or an ASIC or other electrical components. Adapted for coupling engagement with the end of the handle section 10 is a brush attachment 20 or replacement brush serving as brushing or cleaning tool which, as the case may be, can be color coded for its specific user. By means of a coupling device 30 the brush attachment 20 can be mechanically coupled to the handle section 10 in order to transmit the driving motion of the electric motor to the brush head 14 of the brush attachment 20 via a drive shaft 16 mounted in the handle section 10. The coupling device 30 which may be made of one or several parts or portions comprises a positive- or frictional-engagement element for positioning the cleaning tool body in its proper location and, in addition, a drive coupling which transmits the driving motion of the drive to the brush head 14 of the brush attachment 20. Protruding from the end of the handle section 10 is a drive shaft 16 adapted to be driven in a rotating oscillating or rotating fashion by the drive motor 22 via a gearing 12 in a manner equally known in the art, forming an axis of rotation 72. The drive shaft 16 has a coupling portion 32 adapted to receive by positive or frictional engagement therewith a complementary coupling portion of a plug-on shaft 62 arranged in the cleaning tool 20, so that the driving motion is transmitted, enabling the brush head 14 of the brush attachment to be driven in an alternating oscillating manner, oscillating for example at a swivel angle in the range of between plus or minus 10 degrees and plus or minus 60 degrees and at a frequency in the range from 40 to 150 Hz, for example, with an amplitude of between 0.05 mm and 2 mm and a frequency in the range from about 100 Hz to 400 Hz, etc. about an axis of rotation 72 and/or swivel axis 58. Details of the mechanical coupling and the drive or the driving motion or the structural concept of handle section and brush attachment are disclosed in applicant's publications WO 91/07117 (05544), WO 94/12121 (05824), WO 99/20202 (06210), WO 98/01083 (06107), WO 98/47444 (06176), which are hereby incorporated in the disclosure content of the present patent application by express reference.

The control device 18 has an operation inhibiting device 36 or inhibiting means operating, for example, electronically, which inhibits the drive of the handle section 10, particularly the electric motor 22, and enables the drive or permits switching on of the electric motor 22 by means of an ON switch 56 on the handle section 10 only when or after a compatible brush attachment 20 is attached to the handle section 10. The electronic operation inhibiting device 36 is activated and deactivated by means of an enabling element 38 or an enabling function provided on the brush attachment 20. The enabling means or the enabling element 38 can have a coding as a so-called electronic key.

To identify the respectively attached brush attachment 20, provision is made on the handle section 10 for a coding/detecting device or a device for detecting the presence of the enabling element 38. In response to a signal from this device or coding/detecting device, the control device 18 or inhibiting means enables or does not enable the drive or electric motor 22 so that the electric motor 22 can be set in operation by means of the ON switch 56, as the case may be.

Provision is generally made to provide in the brush section or brush attachment 20 a data or information memory, in particular for digital information, which then performs a wireless transmission or exchange of data, that is, without a conductive connection between the brush section and the handle section, with a data or information reader in the handle section 10 of the electrical toothbrush.

Figure 3:
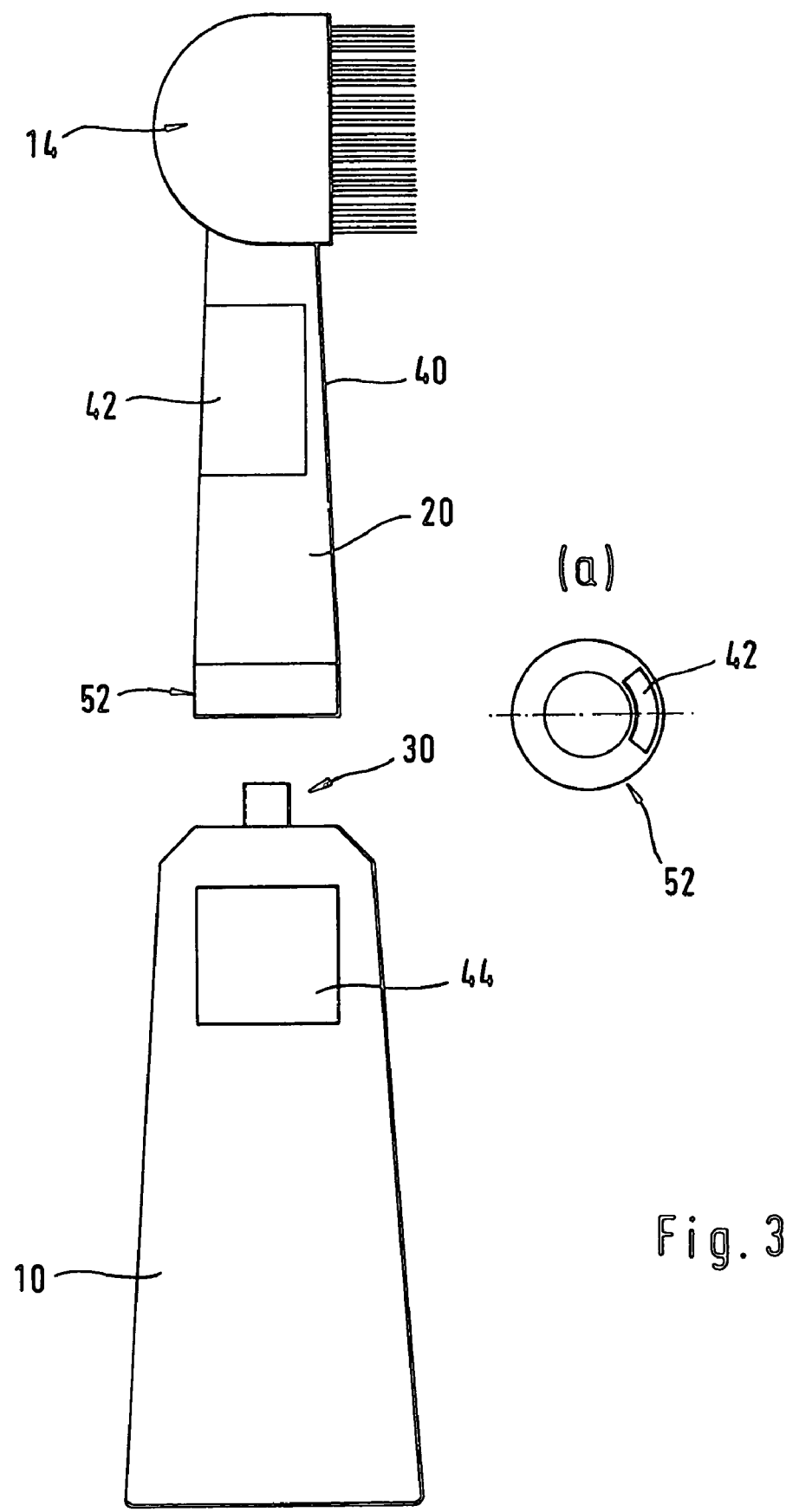
FIG. 3 is a schematic view of an electrical toothbrush having a brush attachment with a transponder adhesive-bonded thereto or integrated therein, and a corresponding detecting device for the non-contacting transmission of data in the handle section.
Figure 4:
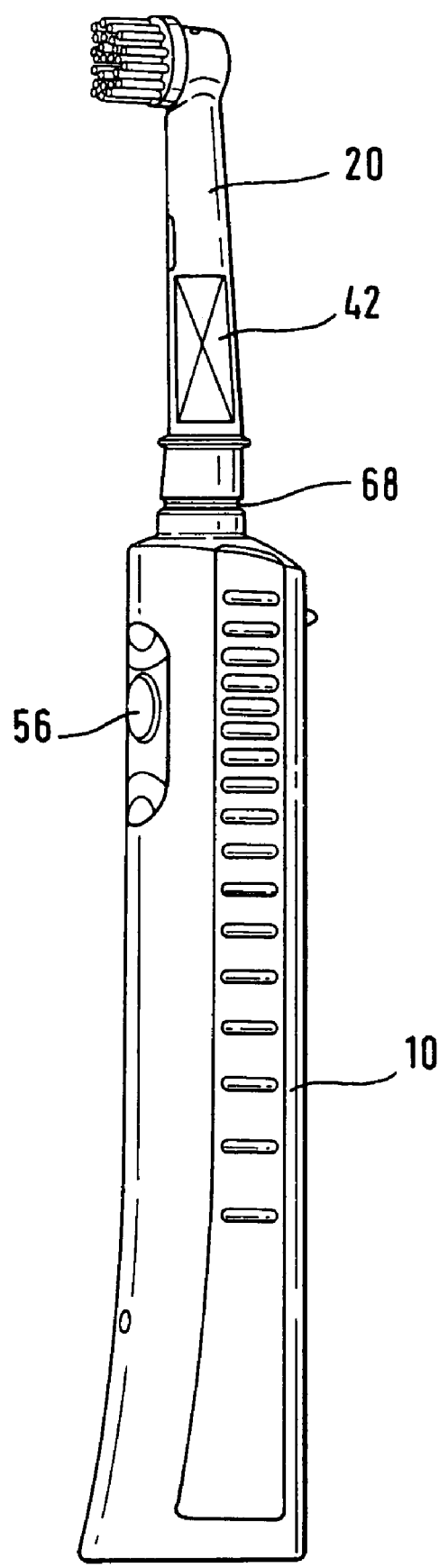
FIG. 4 is a perspective view of the toothbrush of FIG. 3.
Figure 5:
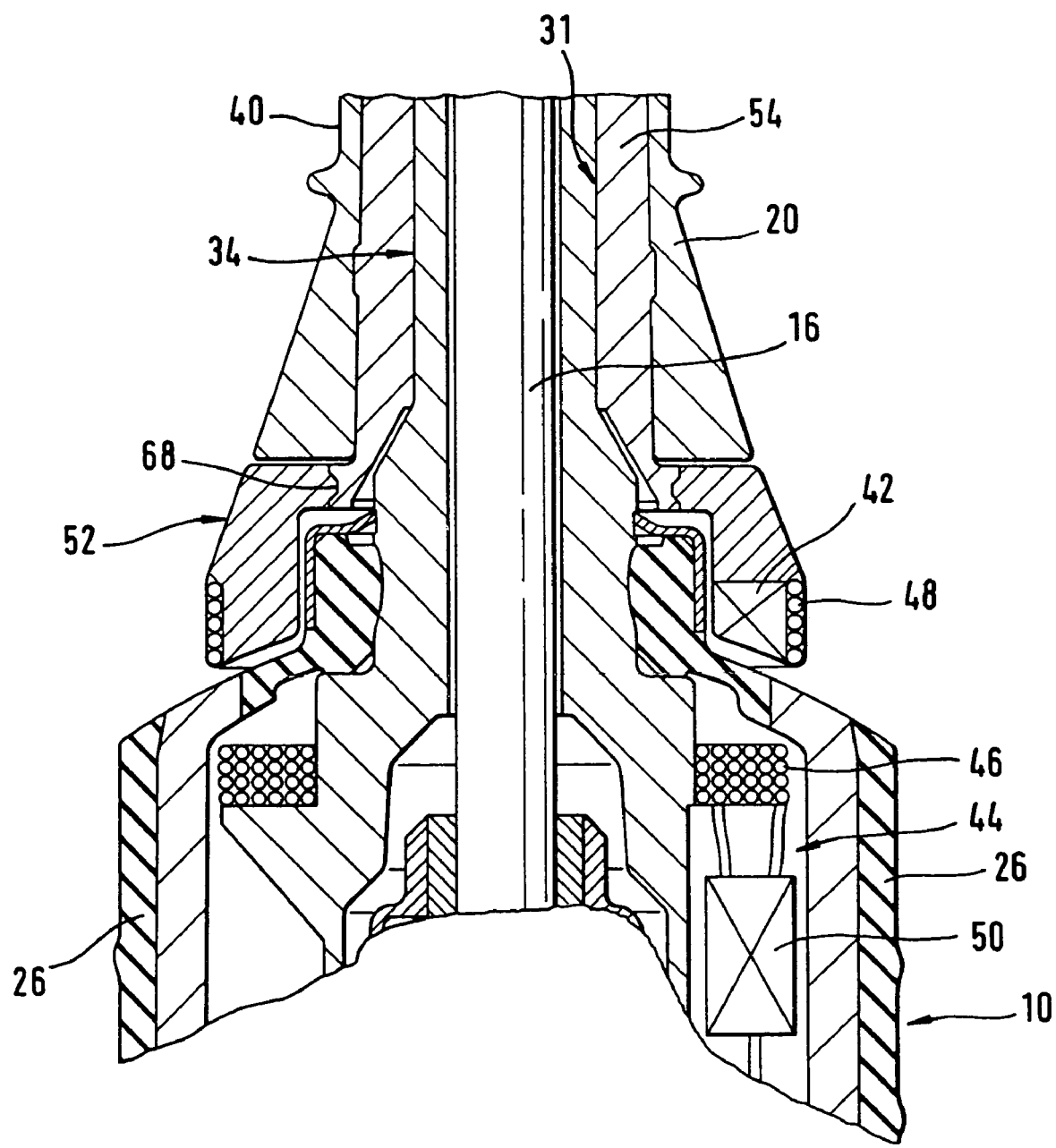
FIG. 5 is a sectional detail view of a toothbrush similar to FIGS. 3 and 4, showing the arrangement of a transponder chip in a coding ring provided at the end of the brush attachment, and a transmitter coil and a receiver coil together with an associated electronic evaluation device in the handle section, with the brush attachment and the handle section being shown in coupled condition.

FIGS. 3 to 5 show an embodiment of an electrical toothbrush according to the invention with wireless data transfer between brush section and handle section, in which the presence of the respective brush attachment 20 coupled to the handle section 10 or properties of the brush attachment 20 are detected or determined via digital signals. For this reason the brush attachment 20 is equipped with a transponder 42 which can be bonded by an adhesive on or to the brush attachment 20 as in the form of a label referred to as smart label (FIG. 4). Advantageously, the transponder 42 may also be contained in the colored slip-on ring 52 at the end of the brush attachment 20 (FIGS. 3 and 5). Provided in the handle section 10 is a detector or reading device 44 which is tuned to the transponder 42 and serves both as a signal transmitter and signal receiver. The detector or reading device 44 in the handle section 10 first transmits electromagnetic waves via the coil 46 to the coil 48 connected to the transponder 42 in order to supply the transponder 42 or its microchip with energy for activation. The transponder 42 stores the energy, is activated and transmits a specific, stored ID or signal or data back to the detector or reading device 44, which receives said ID, signal or data, identifies it by means of an electronic evaluating unit 50 and emits a corresponding signal to the control device 18 or inhibiting device 36 of the handle section 10. The coils 46 and 48 can be operated as both a transmitter and receiver. In a preferred embodiment they are arranged opposite each other at the respective ends of the brush attachment 29 and the handle section 10 (see FIG. 5). The brush attachment 20 can be identified, or its presence on the handle 10 recognized, by means of the ID or data sent back from the transponder 42.

FIG. 6 is a schematic perspective representation of an embodiment of the handle section 10. The handle section 10 has as subassemblies a gearing 12 with drive shaft 16, a control device 18, an electric motor 22 or drive, a power supply such as storage batteries 24 or batteries, and a charging module 28. The preferably water-tight housing 26 enclosing the handle section 10 has been removed in the representation in FIG. 6. The mechanical coupling device 30 to effect coupling engagement between the brush attachment 20 with its brush head 14 and the handle section 10 has a coupling portion 32 on the drive shaft 16 and a coupling portion 34 on the handle section 10. In the present embodiment the inhibiting device 36, the reading device 44 and an electronic evaluating unit 50 are part of the control device 18, which can be configured as an ASIC, for example, and includes a micro-controller or microprocessor and, where applicable, further electronic components or only one discrete circuit. It will be understood, of course, that the electronic components, that is, the control device 18, the inhibiting device 36, the reading device 44 and the electronic evaluating unit 50, can also be implemented by discrete electronic components if required.

Positioned underneath the coupling portion 34 and above the gearing 12 is a coil 46 that is connected, via connecting lines not shown in FIG. 6, to the control device 18 or the reading device 44 and to the electronic evaluating unit 50. In the present embodiment this coil 46 is positioned in the area of a swivel bearing 58 of the handle section 10, which bearing allows the drive shaft 16 to execute a special additional driving motion. For constructive design details, reference is made to the patent application published as WO 98/01083.

From this representation of FIG. 6 as well as that of FIG. 7, showing on an enlarged scale the head end portion of the handle section 10 with the coil 46, which varies in geometry and position from that in FIG. 6, it becomes apparent that the turns of the coil 46 encompass or enclose essentially a longitudinal axis 72 of the handle section 10 or the axis of rotation of the drive shaft 16. Furthermore, from these FIGS. 6 and 7 as well as from FIGS. 8 and 9 it can be seen that the winding plane or turn plane of the coil 46 is aligned essentially perpendicular to the longitudinal axis 72 or the axis of rotation. The individual construction and arrangement of the coil 46 depends not only on the required coupling factors between the coil 46 of the handle section 10 and the coil 48 of the brush attachment 20 but also on the geometrical fitting conditions in the area of the upper portion of the handle section 10. Evidently, therefore, the turn area of the coil 46 can also have, for example, an angle other than a right angle relative to the longitudinal axis 72. It is also possible to accommodate the coil 46 at other positions in the handle section 10 than those shown in the embodiments of FIGS. 6 to 9. The essential point is for the coil 46 to be relatively adjacent or in close proximity to the area of the mechanical coupling device 30 of the handle section 10 while giving due consideration to the individual fitting conditions and geometries. Ultimately the arrangement must be selected so that when the brush attachment 20 is properly mechanically coupled to the handle section 10 the coupling of the coils 46, 48 or the coupling factor is such that data can be transferred between the brush attachment 20 and the handle section 10. With regard to the turn area of the coil 46 it should be noted that said turn area should be chosen as large as possible, again with due consideration to the geometry and fitting conditions on the handle section 10 so that coupling with the enabling function or the enabling element 38 in the brush attachment is optimized or sufficient.

It should also be noted that according to the embodiments of FIGS. 8 and 9 the coil is positioned at the axial height of a plastic sleeve or bearing 60 for the drive shaft 16 in relation to the longitudinal or axis of rotation 72. This bearing 60 or the parts of the handle section 10 positioned in the region of the turn area of the coil 46, for example the drive shaft 16 or other housing parts, can be constructed of ferrite or have constituents made of ferrite, so that this approach, too, can contribute to improving coupling with the enabling element 38 or enabling function of the cleaning and brushing tool or brush attachment 20.

Figure 10:
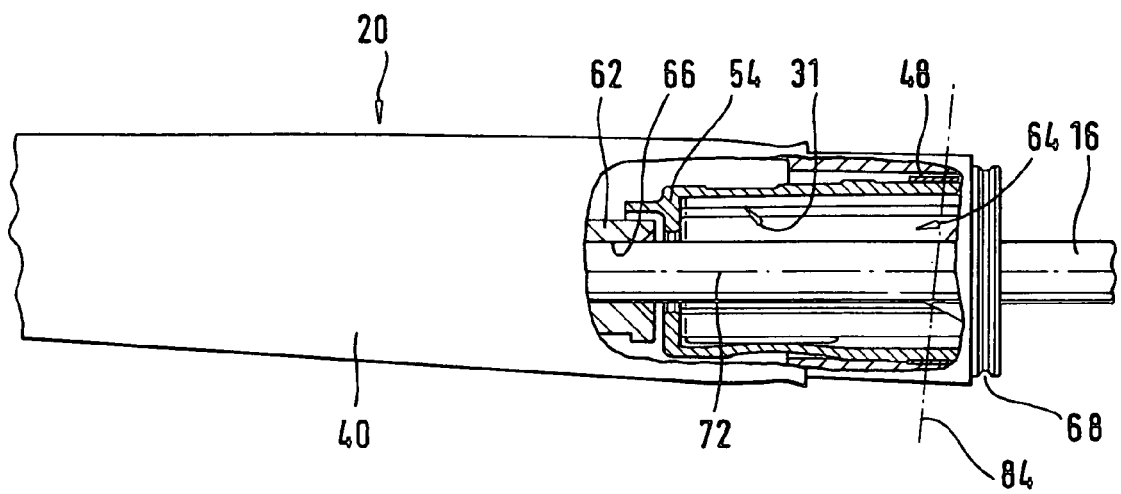
FIG. 10 is a partial view of an embodiment of the brush attachment, showing the wall of the shank partially broken away in the area of a profiled sleeve which is shown in section.
Figure 11:
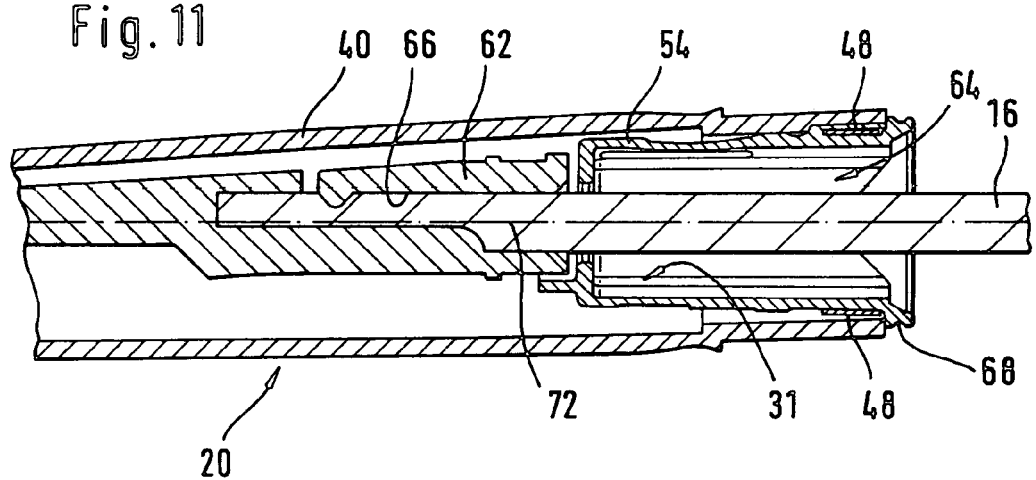
FIG. 11 is a longitudinal sectional view of the brush attachment of FIG. 10.
Figure 12:
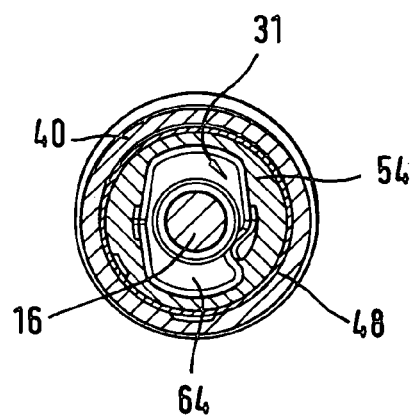
FIG. 12 is a cross-sectional view of the brush attachment of FIG. 10 in the region of the coil, with the section plane being arranged essentially perpendicular to the longitudinal axis or axis of rotation.

FIGS. 10, 11 and 12 show a partial view of the brush attachment 20, presenting among other things a special embodiment of the coupling end portion of the brush attachment 20. For better clarification of the mechanical coupling only the drive shaft 16 is shown, omitting the coupling portion 34 of the handle section 10. The brush attachment 20, in which the data or information memory or the enabling element 38 or an enabling function as, for example, a transponder 42, is accommodated, has a shank 40 that can be constructed as an elongated external mounting tube. Provided in the area of the coupling end of the brush attachment 20 is an annular groove 68 for a colored slip-on ring 52 (FIG. 3), which can be part of a sleeve accommodated in the shank 40. Positioned in the shank 40 at the end close to the coupling is the sleeve, a profiled ring 54 or the like, which has an opening for passage of the shaft 16 to be received in a receiving socket 66 of a plug-on shaft 62. Furthermore, the profiled ring 54 has a receiving socket 64 for the coupling portion 34 of the handle section 10. The plug-on shaft 62 is in a driving connection with the brush head 14 of the brush attachment and transmits the driving motion of the drive shaft 16 of the handle section 10 to the brush head 14. For pertinent details reference is made to German patent application 197 45 876.9, for example, which is hereby incorporated in the disclosure content of the present application by express reference.

From FIGS. 10 to 12 it becomes furthermore apparent that a coil 48 which corresponds with the coil 46 on the handle section 10 is positioned or fixed on the outer wall of the profiled sleeve 54 in the area of the end portion of the brush attachment 20. The turns of the coil 48 encompass the longitudinal axis 72 of the brush attachment 20 or the axis of rotation of the plug-on shaft 62. The turn area of the coil 48 is preferably aligned essentially at right angles to the longitudinal axis 72, but can also enclose an angle other than a right angle with the longitudinal axis 72, as is indicated by the broken line 84. The special construction and arrangement of the coil 48 depends not only on the desired coupling factor with the coil 46 in the handle section 10 but also on the geometrical conditions of the components in the brush attachment 20 and can include in particular angular positions of the turn area ranging between about 40 degrees and 140 degrees relative to the longitudinal axis 72.

Figure 13:
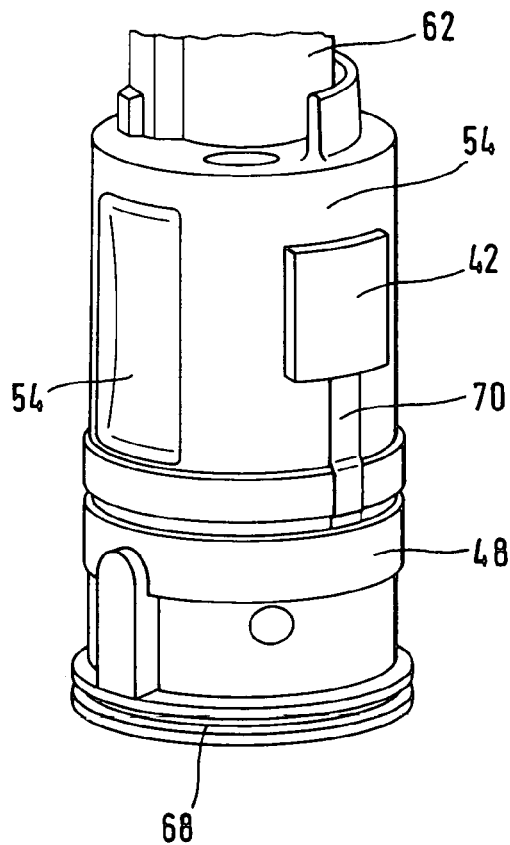
FIG. 13 is a schematic perspective view of the profiled sleeve showing transponder and coil fitted thereto and the adjoining plug-on shaft.
Figure 14A:
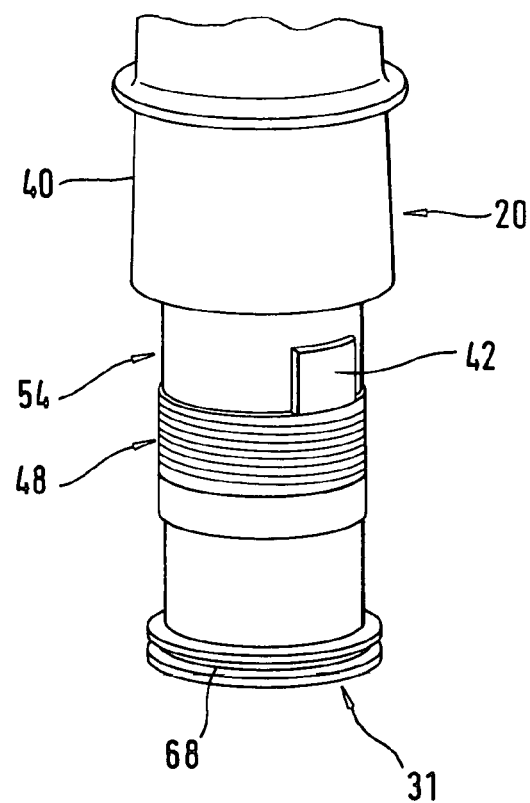
FIG. 14A is a perspective view of the profiled ring with transponder and coil, shown partly withdrawn from the shank of the brush attachment.
Figure 14B:
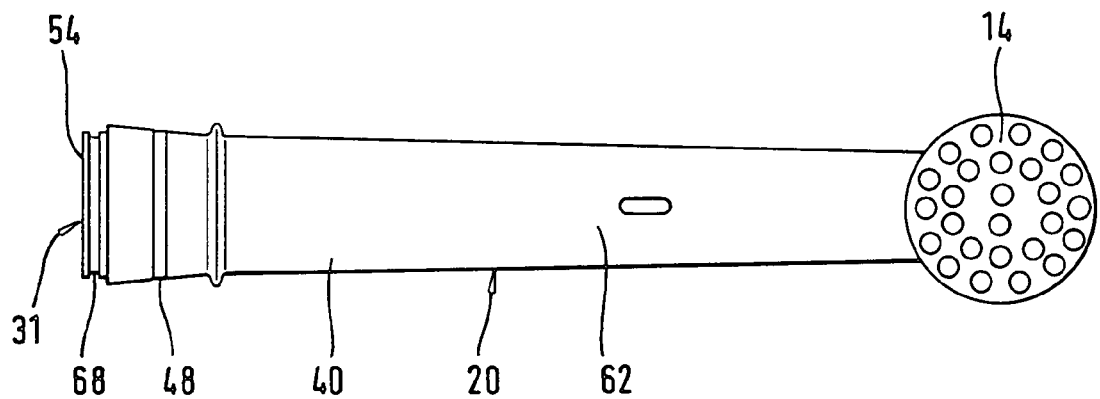
FIG. 14B is a view of the brush attachment showing the coil wound about the shank or tube.

The arrangement of the coil 48 at the profiled ring 54 or a sleeve becomes apparent from the schematic perspective representations of FIGS. 13 and 14. The coil 48 is preferably arranged in the area of the profiled sleeve 54 or profiled ring on the side close to the coupling end and encloses the outer wall of the profiled sleeve 54 in an annular configuration. It is also possible, of course, for the coil 48 to be injection-molded in the plastic profiled sleeve 54 or for the coil 48 to be fastened to the inner wall of the profiled sleeve 54. The data memory or the enabling element 38, which is preferably constructed as a transponder 42, is coupled to the coil 48 either directly (FIG. 14A) or via connecting lines 70. This transponder 42 is likewise fastened to the profiled sleeve 54 or has the plastic material of the profiled sleeve 54 injection-molded around it. Owing to the fact that all the components required for the non-contacting detection of the enabling element or for the data transfer are arranged on or at a separate component of the brush attachment 20, which can be snappingly engaged as with the shank 40, it is possible to test the operation of the enabling element 38 or transponder 42 or coil 48 before assembly or final assembly of the brush attachment 20. FIG. 14B shows another embodiment of the brush attachment 20 or arrangement of the coil 48. In this embodiment the coil 48 is fastened to the tube or shank 40 of the brush attachment 20, preferably to the outer wall. In detail, in the area of the mating coupling device or in a lower end area facing away from the brush head 14 the coil is wound onto the tube 40. The terminals of the coil 48 are connected to the transponder not shown in FIG. 14B.

Figure 15:
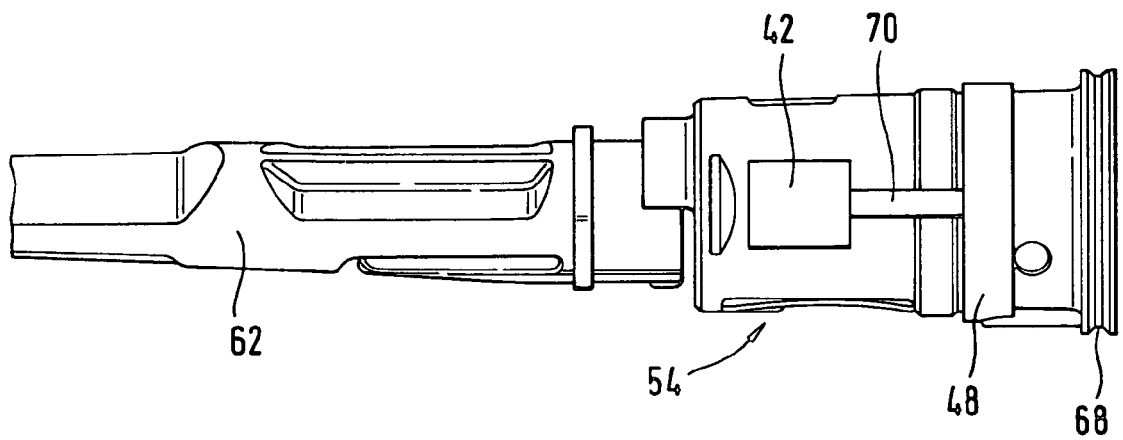
FIG. 15 is a side view of the profiled ring with transponder and coil and portions of the plug-on shaft of the brush attachment.
Figure 16:
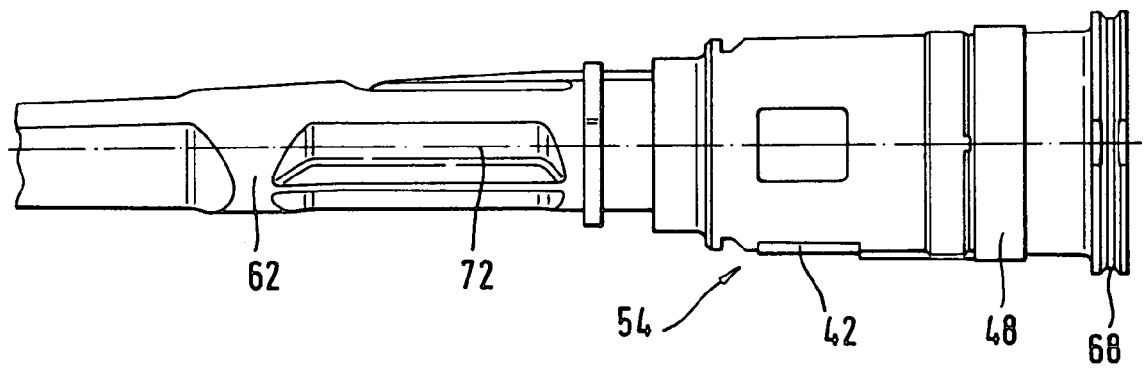
FIG. 16 is a view of the arrangement of FIG. 15, but turned through an angle of about 90 degrees.
Figure 17:
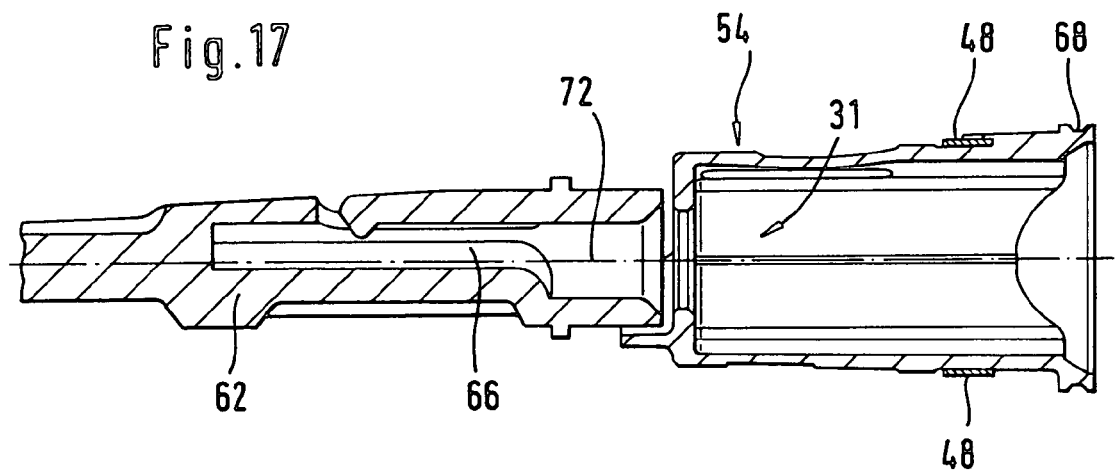
FIG. 17 is a sectional view of the arrangement of FIG. 15, but turned through an angle of about 180 degrees.

FIGS. 15, 16 and 17 show in another representation the arrangement and position of the parts of the brush attachment 20 required for the enabling function. As such FIGS. 15 to 17 show only the ring, sleeve or profiled sleeve 54 and a part of the plug-on shaft 62 of the brush attachment 20. Again it can be seen that the coil 48 encloses the profiled sleeve 54 in an essentially annular, particularly circular-ring shaped configuration, and is fastened to an outer wall of the profiled ring 54. FIG. 15 also shows the relative arrangement of transponder 42, connecting line 70 and coil 48.

Figure 18:
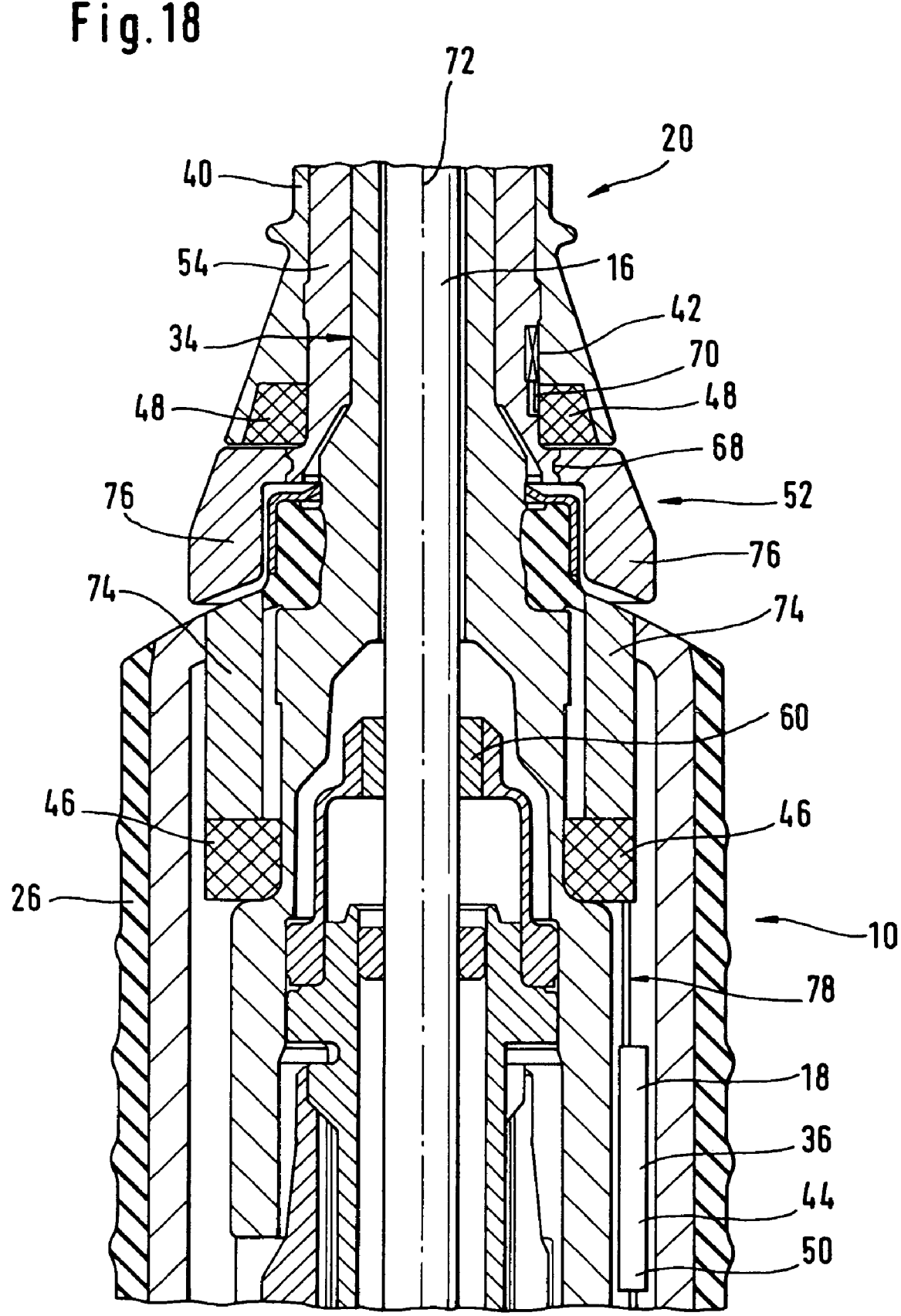
FIG. 18 is a representation similar to FIG. 5, showing a modified arrangement of the coils and ferrite bodies being provided to improve the coupling factor of the coils.

FIG. 18 shows a partial view of the mechanically coupled handle section 10 and the brush attachment 20. In this embodiment the coil 48 is positioned in the end portion of the shank 40, with the transponder 42 and the connecting lines 70 being arranged on the inner wall of the tubular shank 40, for example. The coil 46 on the handle section 10 is set slightly further inside than in the previous embodiments and is connected via connecting lines 78 to the control device 18 or the inhibiting device 36 or the reading device 44 or the electronic evaluating unit 50. To improve the coupling factor between the coil 46 and the coil 48 it is possible to provide ferrite bodies 74, 76 in the handle section 10 and/or the brush attachment 20, which thus improve the coupling factor between the coils 46, 48 and permit where necessary a bigger constructively predetermined gap between the coils 46, 48.

From this showing, too, it becomes apparent that the coils 46, 48 enclose with their turns the longitudinal axis 72 or axis of rotation, and further that preferably the turn area of the coils 46, 48 is arranged essentially perpendicular to the longitudinal axis 72.

Basically it is possible for the coils 46, 48 to be positioned in any position on the handle section 10 and, respectively, the brush attachment 20, provided adequate coupling between the coils 46, 48 exists when the brush attachment 20 is mechanically coupled correctly to the handle section 10 so that the control device provided in the handle section 10 can communicate with or receive data from the enabling element 38 or transponder 42 provided in the brush attachment 20 via an electric and/or magnetic, in particular inductive coupling.

Figure 19:
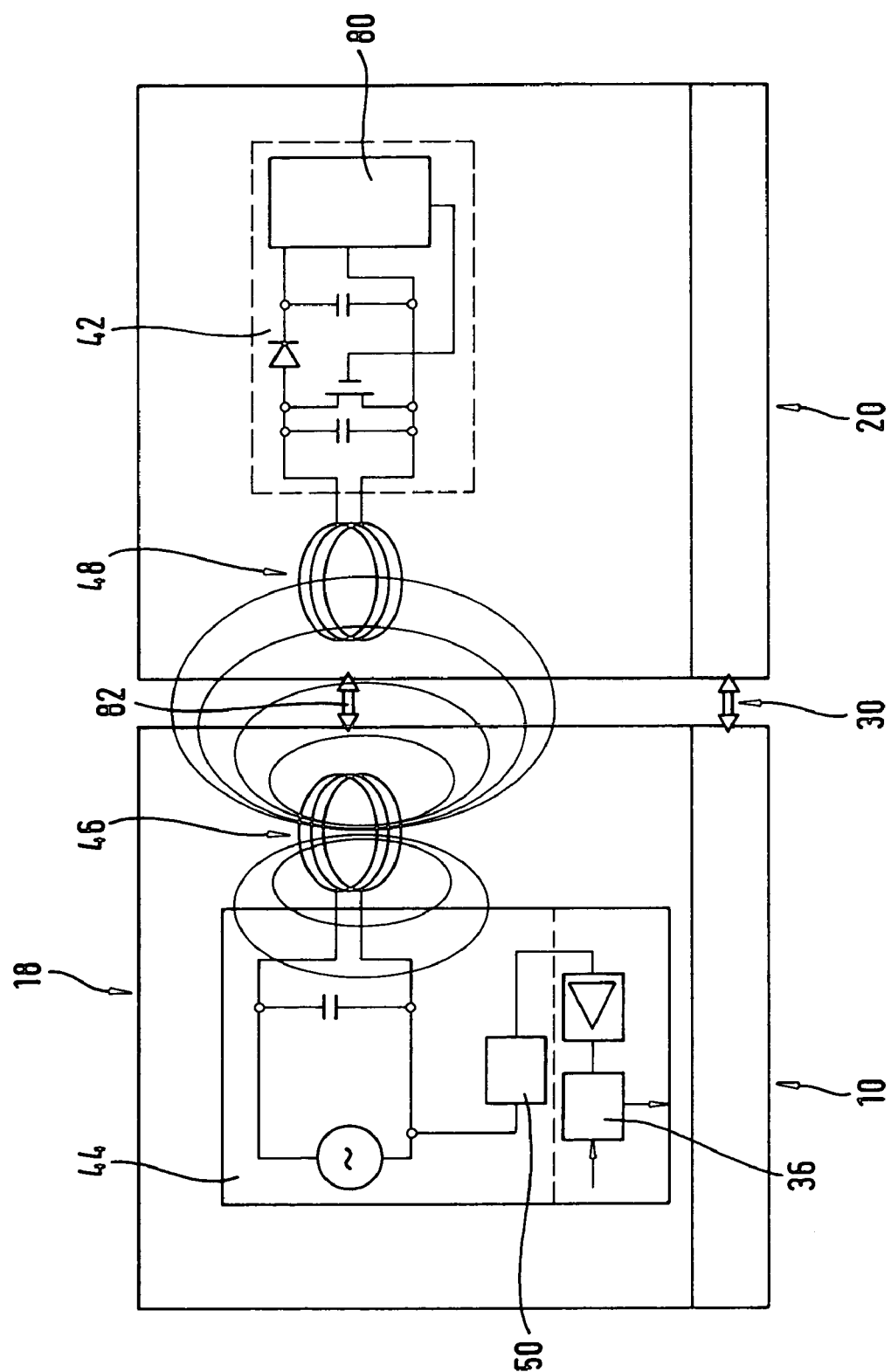
FIG. 19 is a schematic view, in the form of a block diagram, of the control device with reading device, electronic evaluating unit and operation inhibiting device as component parts of the handle section, and the transponder as a component part of the brush attachment, with the handle section and the brush attachment being coupled for communication.

FIG. 19 shows in a schematic block diagram the handle section 10 and the brush attachment 20, which are interconnectable via a mechanical coupling device 30 to establish a driving connection. In addition, the brush attachment 20 and the handle section 10 are in a condition of non-contacting data transfer or communication exchange via an electric, magnetic or electromagnetic, in particular inductive coupling 82 when the brush attachment 20 is mechanically coupled to the handle section 10. The basic architecture of a control device 18 or a reading device 44 as well as of the enabling element 38 or transponder 42 is generally known. In this context, reference is made to the text book "RFID-Handbuch, Grundlagen und praktische Anwendung induktiver kontaktloser Chipkarten" by Klaus Finkenzeller, 2nd edition, November 1999, Karl Hansa Verlag München, ISBN 3-446-2278-7, in particular to chapter 3, which is hereby incorporated in the disclosure content of the present application by express reference. Provided in the handle section 10 is the control device 18 with reading device 44, which includes the coil 46, a capacitor as resonant circuit and a generator that operates this resonant circuit at roughly its resonant frequency, for example in the range of between 13 and 14 megahertz, for example at 13.56 megahertz or also at 125 kilohertz, plus or minus 10 kilohertz. Connected to this circuit arrangement is the electronic evaluating unit 50 whose signals, amplified if necessary by means of an amplifier, are fed to the inhibiting device 36. Further signals can be fed to the inhibiting device 36 as input values if so required. An output signal of this inhibiting device 36 is used to enable or inhibit the drive of the handle section 10 of the toothbrush, depending on whether the presence of the enabling element 38 of the brush attachment 20 is detected as being mechanically coupled correctly to the handle section 10 or a corresponding data transfer has taken place or not.

Provided in or on the brush section or brush attachment 20 is the coil 48, to which a capacitor is connected. The two components likewise form a resonant circuit which is tuned to the transmit or resonant frequency of the resonant circuit of the reading device 44. Also provided are a rectifier, for example, a diode, and an energy storage device, for example, a capacitor, which supply the transponder 42, which is of the passive type in the present embodiment, with the energy necessary to operate the transponder, drawn from the high-frequency electromagnetic field radiated by the coil 46. It is also possible for a micro-controller 80 to be provided in the transponder 42, which at least partly opens and closes a switching device inserted parallel to the resonant circuit capacitor or coil 48, for example, a FET, as a load resistor of the transponder resonant circuit. The clock frequency of these opening and closing cycles can lie, for example, in the 1 kHz to 100 kHz range, for example, at about 5 kHz, about 20 kHz or at about 212 kHz. By providing for switching on and off (modulating) of the load resistor in the transponder 42 at a clock frequency lying far below the resonant frequency, there arise in the reading device 44 sidebands adjacent to the transmit or resonant frequency of the resonant circuit of the reading device 44, which can be readily detected with a bandpass filter, for example, resulting in an improved signal-to-noise ratio. It is also possible, preferably at low clock frequencies in the range between 1 kHz and 50 kHz, to use an envelope demodulator or the like for demodulation. With this clock frequency it is also possible to transmit a multiplicity of data from the transponder 42 to the reading device 44, the data being defined by the clock rate or pulse train, the pulse duty factor or the pulse repetition frequency. Ultimately these approaches amount to a load modulation by means of a subcarrier on the transponder 42, as the result of which the reaction of the transponder 42 to the reading device 44 can be simply and easily detected by means of known demodulation processes (for example, amplitude shift keying (ASK) with and without sideband). For further details reference is made to the previously mentioned RFID manual. Furthermore, the reading device will have to be adapted accordingly if there is no load modulation of the transponder resonant circuit and the phase (phase shift keying) or frequency (frequency shift keying) is modulated.

Data for implementing advantageous embodiments of the transfer system between the brush attachment 20 and the handle section 10 will be given below by way of example. With a view to obtaining practicable coupling factors between the data memory in the brush attachment and the data reader in the handhold it has proven advantageous for the coils 46, 48 connected to the data memory and data reader for the wireless transfer of data to be arranged at a geometrical position roughly in the lower third of the shank 40 of the brush attachment 20 at the coupling end and in the upper quarter of the housing 26 of the handle section 10 at the coupling end. The closer the two coils 46, 48 are arranged relative to each other when the handle section and brush attachment are properly coupled, the easier it is to achieve the required coupling factors. The coupling factors are also dependent on the projection of the congruent turn areas of the two coils 46, 48. As such it makes sense for the inclination of the turn areas of the coils relative to the longitudinal axis 72 or axis of rotation of the brush section and handle section not to deviate by more than about 50 degrees from the common, optimal right-angled position. Preferably, the turns of the coils 46, 48 encompass or enclose the longitudinal axis 72 or axis of rotation of the handle section and the brush section, thereby achieving an adequate coupling between the coils 46, 48 in addition to enabling a geometrically practicable installation site to be chosen in the brush section and/or the handle section. The coils themselves can be conventional, wire-wound coils, with the exemplary data for coil 46 being about 10, plus or minus 3 turns at a turn diameter of about 15, plus or minus 3 mm and a wire thickness of about 0.1 mm. The inductance can lie in the range of 2 µH, approximately, and the ohmic resistance in the range of 1 ohm. For coil 48, 15 plus or minus 4 turns at a turn diameter of 9 plus or minus 2 mm and a wire thickness of, for example, 0.06 mm can be provided. The inductance then lies in the range of about 2 µH to about 8 µH, preferably at about 5 µH at an ohmic resistance of the coil of about 1 ohm to about 10 ohm, preferably about 4 ohm. It will be understood, of course, that the coils 46, 48 can be constructed as conventional wire-wound coils or, alternatively, in the form of turns printed, for example, on a flexible plastic foil or on the transponder chip itself. The coupling of the two coils 46, 48 with properly mechanically coupled handle section and brush section can lie between 1 percent and 8 percent, preferably at about 5 percent, the coupling of the coils 46, 48 being primarily of the inductive type in the present embodiment and with the frequencies in the two-digit MHz range therein employed. The diameter of the coils should not be less than 3 mm, approximately. The previously mentioned data, given by way of example, for the dimensions and geometrical configuration of the coils does not apply to the use of ferrite bodies 74, 76 in accordance with FIG. 18. When allowance is made for such ferrite bodies 74, 76 for improving the coupling of the coils 46, 48 the above data can be modified accordingly. The quality factor of the transponder resonant circuit should be between about 5 and 15, preferably between about 8 and 10, in order to minimize the dependence on tolerance-related fluctuations of the resonant frequency, particularly with regard to the phase shift. The quality factor is defined, among other things, by the wire thickness of the coil 48.

The data or information memory of the brush section, in particular transponder 42, and the data or information reader 44 in the handhold of the electrical toothbrush are commercially available as standard items in a wide variety of different specifications. For pertinent details reference is again made to the previously mentioned RFID manual. It is also possible, of course, to include the data reader 44 in a user-specific integrated circuit (ASIC) provided in the handle section of the toothbrush.

LIST OF REFERENCES 10 handle section
12 gearing
14 brush head
16 drive shaft
18 control device, control function (with microprocessor, etc.)
20 brush attachment, brush section
22 electric motor, drive mechanism
24 storage battery
26 housing
28 charging module
30 coupling device
31 mating coupling device
32 coupling portion
34 coupling portion
36 operation inhibiting device, operation inhibiting function (part of 18)
38 enabling element, enabling function
40 shank, tube
42 transponder
44 reading device, reading function (part of 18)
46 coil (handle section)
48 coil (brush attachment)
50 electronic evaluating unit, evaluating function (part of 18)
52 slip-on ring
54 profiled ring, profiled sleeve
56 ON switch, switch-on function
58 swivel bearing, swivel axis
60 bearing
62 plug-on shaft
64 receiving socket (for 34)
66 receiving socket (for 32)
68 annular groove (for 52)
70 connecting line
72 longitudinal axis, axis of rotation
74 ferrite body
76 ferrite body
78 connecting line
80 microcontroller
82 inductive coupling
84 line

What is claimed is:

1. A toothbrush, comprising: a brushhead portion having a bristle section in the vicinity of one end thereof;
a handle portion, with a driver assembly therein for driving the bristle section, wherein the brushhead portion and the handle portion are adapted such that the brushhead portion is removable from the handle portion;
communication means for data communication between the brushhead portion and the handle portion when the brushhead portion and handle portion are joined together;
a memory element in the brushhead portion for storing at least data which identifies the brushhead portion, the memory element having the capability of information being written to the memory element;
and a microcontroller in the handle portion, wherein the memory element in the brushhead portion provides information therein to the microcontroller via the communication means.

2. A toothbrush of claim 1, wherein the information stored in the memory element includes an identification number associated with the brushhead, wherein the microcontroller in operation accumulates information concerning use of the brushhead.

3. A toothbrush of claim 1, wherein the information is operating information for the operation of the toothbrush for the brushhead.

4. A toothbrush of claim 1, wherein the memory element can store information concerning use of the toothbrush.

5. A toothbrush of claim 1, wherein the toothbrush will not operate unless the information from the memory element is valid, as determined by the microcontroller.

6. A toothbrush of claim 1, including a plurality of interchangeable brushheads, further including means for displaying user-specific information.

7. A toothbrush of claim 1, further including a device for providing operating information to a brushhead to define particular operations thereof.

8. A toothbrush of claim 1, wherein the communication means includes electrically conductive elements.

9. A toothbrush of claim 1, wherein the communication means comprise wireless components.

10. A toothbrush of claim 9, wherein the wireless components include coils on the brushhead and the handle for inductive communication.

11. A toothbrush of claim 1, wherein the microcontroller includes means for evaluating the time of past uses of the brushhead.

12. A brushhead portion of a toothbrush, the toothbrush including a handle portion to which the brushhead portion can be joined comprising:
a brushhead assembly which includes a bristle section, the brushhead assembly adapted to be removable from the handle portion of the toothbrush;
communication means for data communication between the brushhead assembly and a separate device;
and a memory element in the brushhead assembly for storing data identifying the brushhead assembly, the memory element having the capability of information being written to the memory element.

13. A brushhead of claim 12, wherein said separate device is the handle portion of the toothbrush.

14. A brushhead of claim 12, wherein the communication means includes means for data communication with the handle portion when the brushhead assembly and the handle are joined together.

15. A brushhead of claim 12, wherein the information is operating information for proper operation of the toothbrush relative to said brushhead assembly.

16. A brushhead of claim 12, wherein the communication means includes electrically conductive elements.

17. A brushhead of claim 12, wherein the wireless components include coils for inductive communication.

18. A brushhead of claim 12, wherein the communication means comprises wireless components.

19. A toothbrush, comprising: a brushhead portion having a bristle section in the vicinity of one end thereof;

a handle portion, with a driver assembly therein for driving the bristle section, wherein the brushhead portion and the handle portion are adapted such that the brushhead portion is removable from the handle portion;

communication means for data communication between the brushhead portion and the handle portion when the brushhead portion and handle portion are joined together;

a memory element in the brushhead portion for storing at least data which identifies the brushhead portion;

a microcontroller in the handle portion, wherein the memory element in the brushhead portion provides information therein to the microcontroller via the communication means; and a plurality of interchangeable brushheads, further including means for displaying user-specific information.

20. A toothbrush, comprising: a brushhead portion having a bristle section in the vicinity of one end thereof;

a handle portion, with a driver assembly therein for driving the bristle section, wherein the brushhead portion and the handle portion are adapted such that the brushhead portion is removable from the handle portion;

communication means for data communication between the brushhead portion and the handle portion when the brushhead portion and handle portion are joined together, a memory element in the brushhead portion for storing at least data which identifies the brushhead portion; and a microcontroller in the handle portion, wherein the memory element in the brushhead portion provides information therein to the microcontroller via the communication means, wherein the microcontroller includes means for comparing the actual use of the brushhead against a certain maximal cleaning period and for providing an indication when the certain maximal cleaning period has been met, indicating that the brushhead should be replaced.

* * * * *

UNITED STATES PATENT AND TRADEMARK OFFICE
CERTIFICATE OF CORRECTION

PATENT NO. : 7,207,080 B2
APPLICATION NO. : 10/241274
DATED : April 24, 2007
INVENTOR(S) : Hilscher et al.

Page 1 of 1

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 1227 days Delete the phrase "by 1227 days" and insert -- by 822 days --

Signed and Sealed this

Twenty-first Day of July, 2009

JOHN DOLL
*Acting Director of the United States Patent and Trademark Office*